(12) United States Patent
Gaertner et al.

(10) Patent No.: US 9,198,974 B2
(45) Date of Patent: Dec. 1, 2015

(54) DECORATED MACROMOLECULAR SCAFFOLDS

(75) Inventors: Hubert Gaertner, Archamps (FR); Oliver Hartley, Carouge (CH)

(73) Assignee: Mintaka Foundation for Medical Research, Geneva (CH)

( * ) Notice: Subject to any disclaimer, the term of this patent is extended or adjusted under 35 U.S.C. 154(b) by 0 days.

(21) Appl. No.: 14/111,840

(22) PCT Filed: Apr. 11, 2012

(86) PCT No.: PCT/GB2012/050792
§ 371 (c)(1),
(2), (4) Date: Mar. 6, 2014

(87) PCT Pub. No.: WO2012/140418
PCT Pub. Date: Oct. 18, 2012

(65) Prior Publication Data
US 2014/0221569 A1    Aug. 7, 2014

(30) Foreign Application Priority Data

Apr. 12, 2011    (GB) .................................. 1106203.1

(51) Int. Cl.
*A61K 47/48*    (2006.01)
*C08G 83/00*    (2006.01)
*C08G 85/00*    (2006.01)

(52) U.S. Cl.
CPC ..... *A61K 47/48207* (2013.01); *A61K 47/48215* (2013.01); *C08G 83/002* (2013.01); *C08G 85/004* (2013.01)

(58) Field of Classification Search
CPC ................. A61K 47/78207; A61K 47/48215; C08G 83/002; C08G 85/004
USPC ............ 514/1.1, 772.1, 772.3; 525/54.1, 451; 528/392; 977/754
See application file for complete search history.

(56) References Cited

PUBLICATIONS

Mitchell, J.P., et al.; Bioorganic & Medicinal Chemistry Letters, 1999, p. 2785-2788.*
Boswell et al., "Synthesis, characterization, and biological evaluation of integrin alpha v beta 3-targeted PAMAM dendrimers", Molecular Pharmaceutics, 2008, vol. 5, 527-539.
Kono et al., "Preparation and cytotoxic activity of poly(ethylene glycol)-modified poly(amidoamine) dendrimers bearing adriamycin", Biomaterials, 2008, 29, 1664-1675.
Dirksen et al., "Nucleophilic catalysis of oxime ligation", Angew Chem Int Ed, 2006, 45, 7581-7584.
Dirksen et al., "Nucleophilic catalysis of hydrazone formation and transimination: implications for dynamic covalent chemistry", Journal of the American Chemical Society, 2006, 128, 15602-15603.

* cited by examiner

*Primary Examiner* — Robert Jones, Jr.
(74) *Attorney, Agent, or Firm* — Klauber & Jackson LLC

(57) ABSTRACT

The present invention relates to a method for preparing decorated macromolecular scaffolds. The method of the invention is useful for the generation of bioactive nanoparticles for use in clinical applications. Such applications include drag and gene delivery, tumour targeting, bioimaging, tissue remodelling, generation of antiviral products and vaccines delivery.

9 Claims, 12 Drawing Sheets

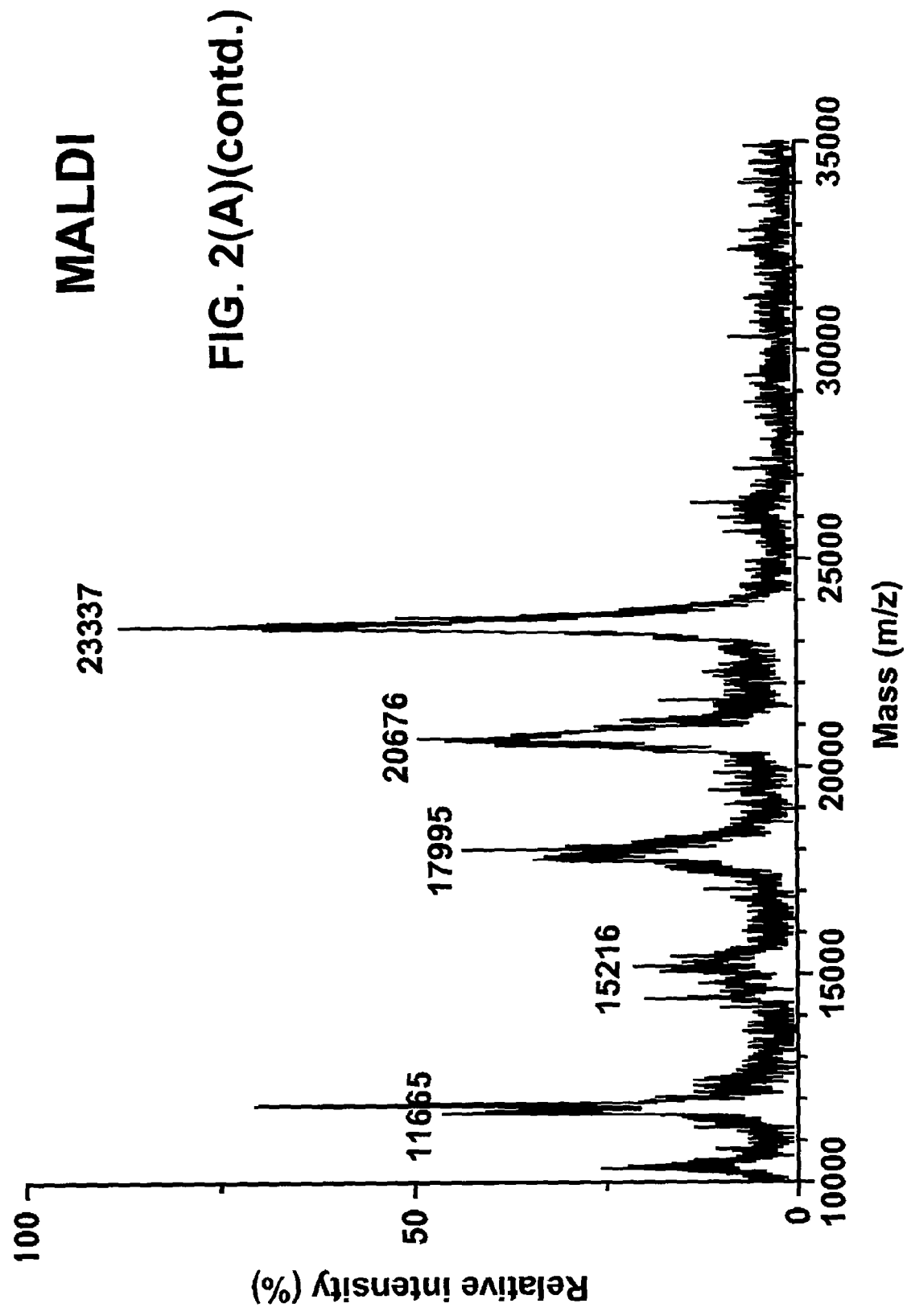

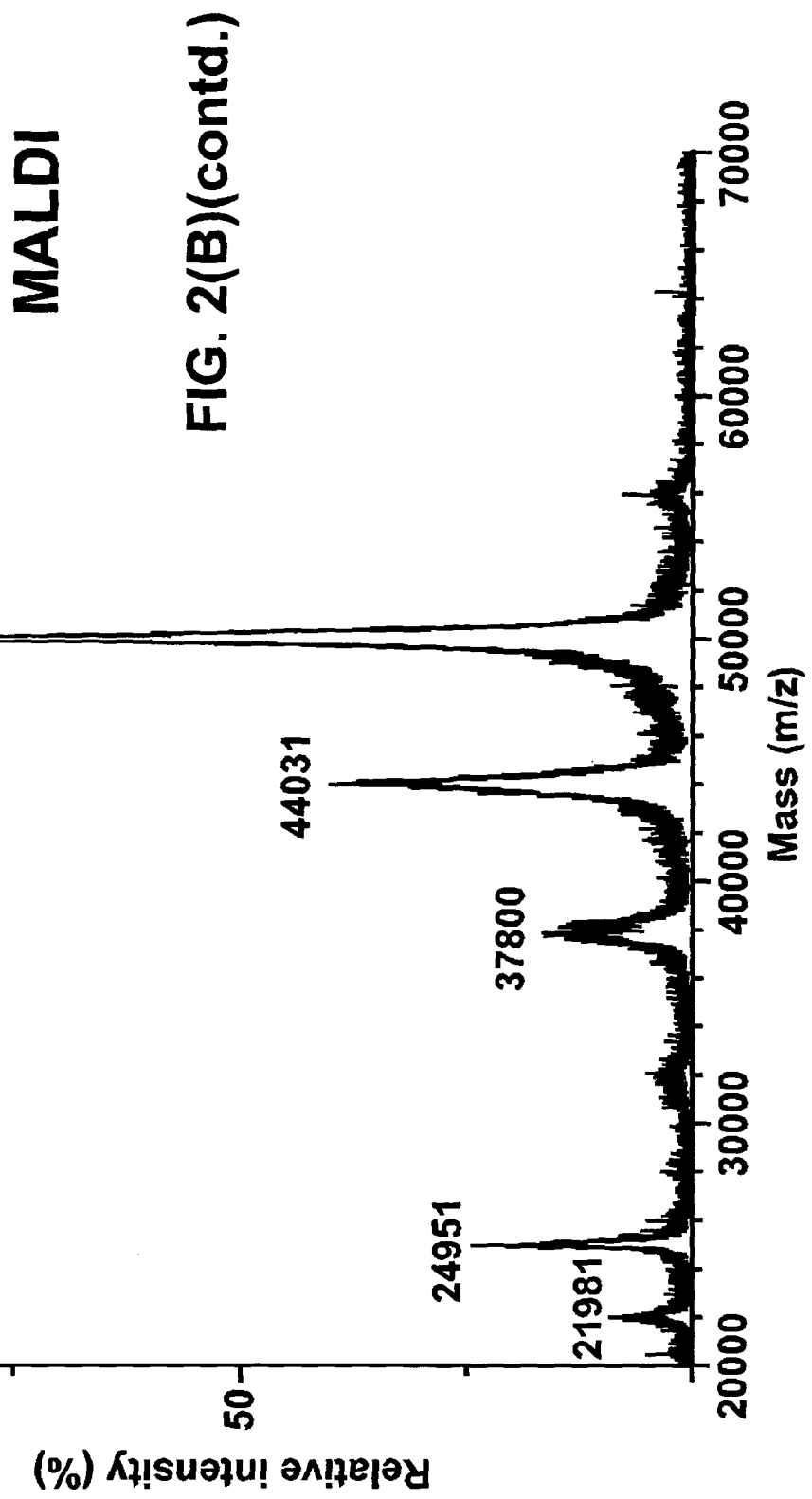
FIG. 2(B)(contd.)

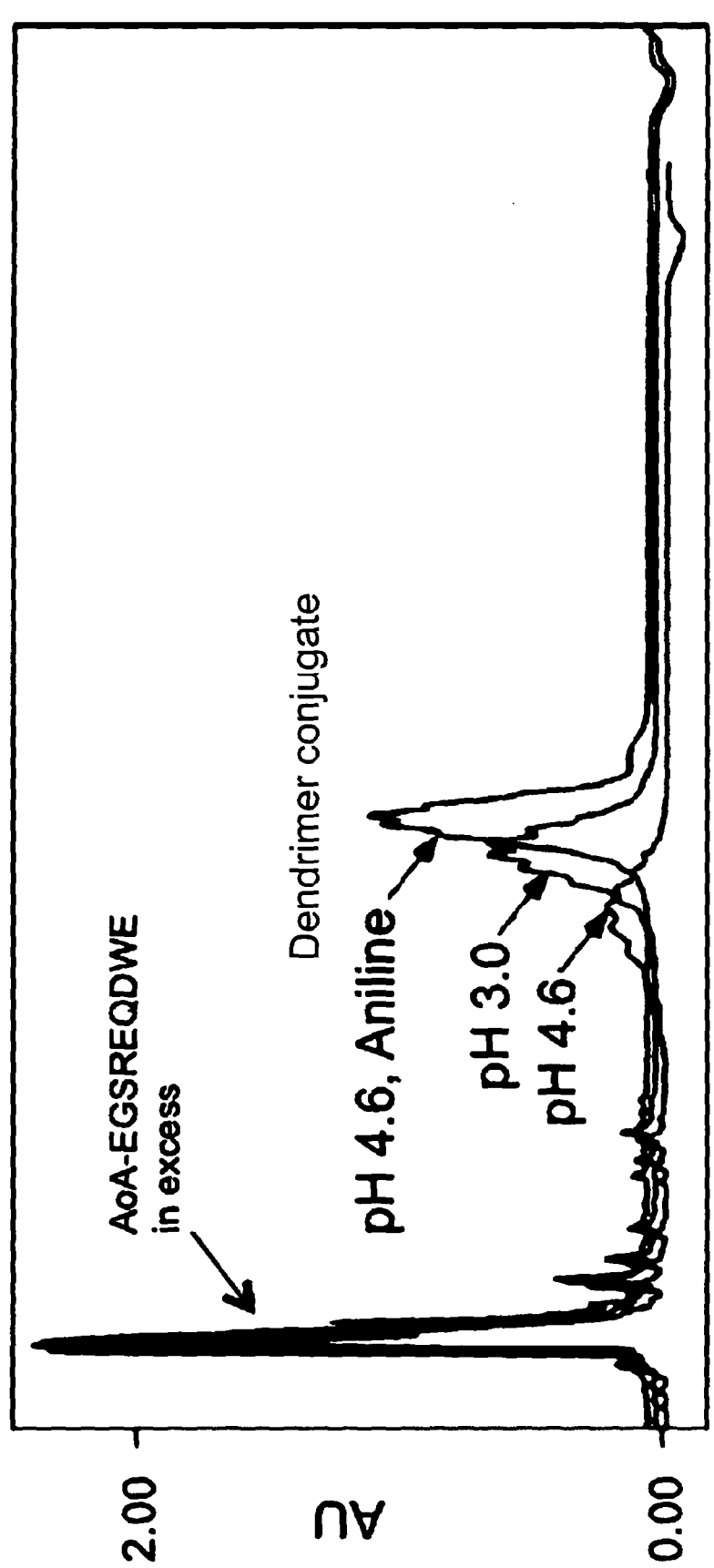

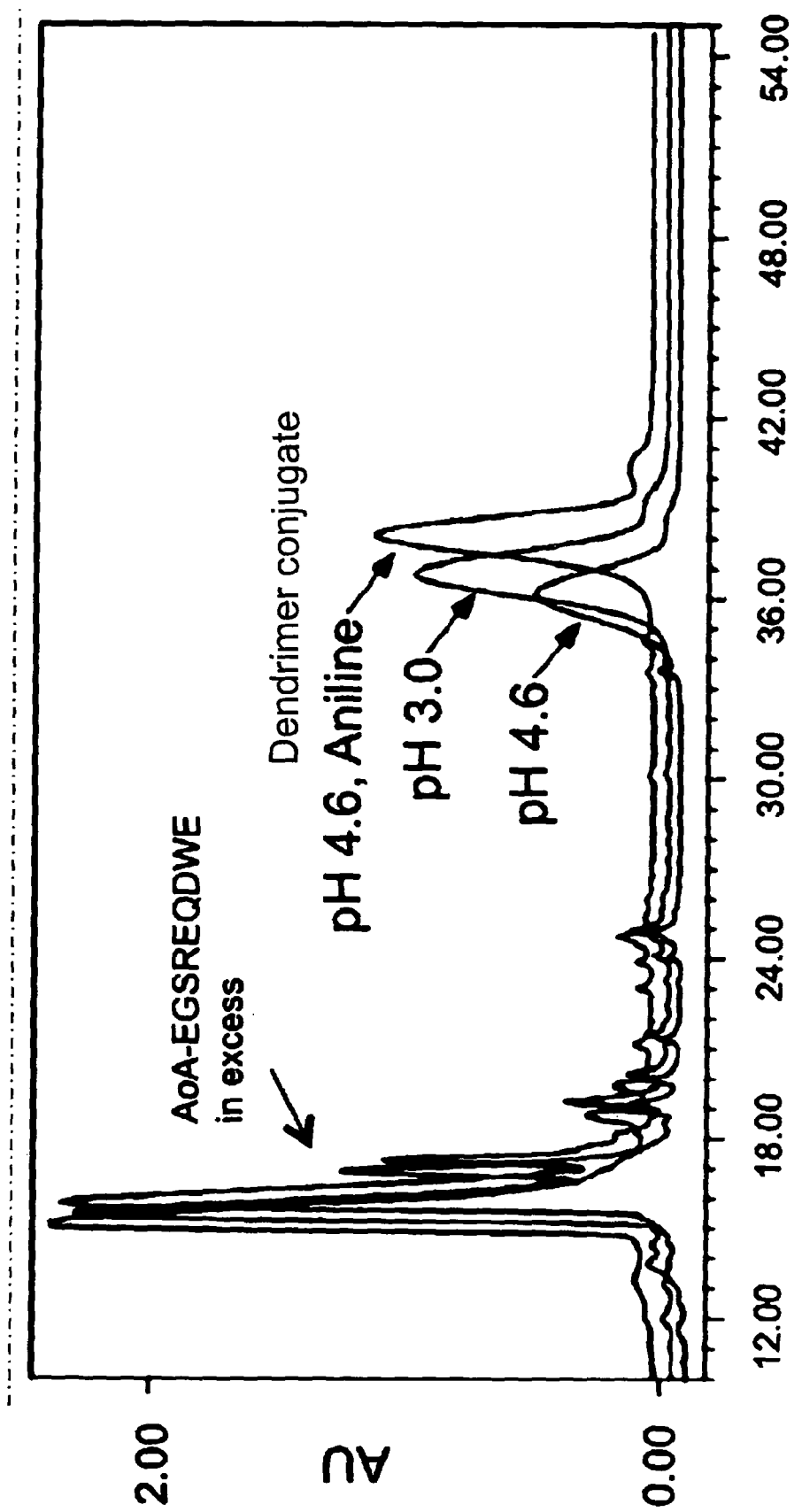

DECORATED MACROMOLECULAR SCAFFOLDS

CROSS REFERENCE TO RELATED APPLICATIONS

The present application is a National Stage Application claiming the priority of co-pending PCT Application No. PCT/GB2012/050792 filed Apr. 11, 2012, which in turn claims priority from Great Britain Application No. 1106203.1 filed Apr. 12, 2011. Applicants claim the benefits of 35 U.S.C. Section 120 as to the PCT application and priority under 35 U.S.C. Section 119 as to the said U.S. Provisional application, and the entire disclosures of both applications are incorporated herein by reference in their entireties.

BACKGROUND

The present invention relates to a method for preparing decorated macromolecular scaffolds. More particularly, the invention relates to a method for preparing molecular scaffolds decorated with ligands and with a high degree of decoration. The method of the invention is useful for the generation of bioactive nanoparticles for use in clinical applications. Such applications include drug and gene delivery, tumour targeting, bioimaging, tissue remodelling, generation of antiviral products and vaccines delivery.

Bioactive nanoparticles are nanoparticles carrying biologically active ligands (for example drugs, peptides, and vaccines). Bioactive nanoparticles are much smaller than human cells but are similar in size to large biomolecules such as enzymes and receptors and can therefore easily enter most cells, and move in and out of blood vessels enabling them to circulate through the body. Bioactive nanoparticles are attractive candidates for use as targeted drug delivery vehicles. Bioactive nanoparticles are based on nanoparticles such as liposomes, micelles, macromolecular scaffolds such as dendrimers, nanolipospheres, silica-coated micelles and ceramic nanoparticles.

Bioactive nanoparticles comprised of random polymers having ligands conjugated onto the random polymer can be readily produced. However the conjugation of ligands onto macromolecular scaffolds, for example dendrimers, has proved to be more difficult.

Dendrimers are macromolecular scaffolds with a well-defined highly branched structure carrying a number of reactive surface groups. The number of surface groups on a macromolecular scaffold is referred to as the valency of the macromolecular scaffold. The highly branched structure is the result of an iterative synthetic process starting from a central core which is extended outwards by a series of reactions which result in the branching structure. The scheme below represents a central core with a valency of four. Each iterative synthetic step doubles the number of surface groups.

Scheme 1 - iterative synthetic process

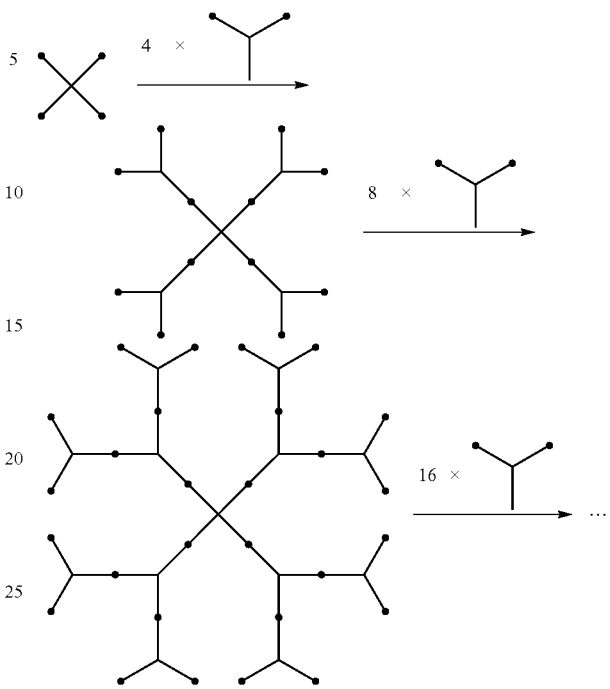

The number of branch points encountered upon moving outwards from the core to the surface groups of the dendrimer define the generation of the dendrimer. G-0 refers to a generation zero dendrimer. Thus, in scheme 1, the G-0 dendrimer has four surface groups (i.e. a tetramer), the G-1 surface group has eight surface groups (i.e. an octamer) and the G-2 dendrimer has 16 surface groups. In this example, the number of surface groups doubles with each branching step, but introduction of a trivalent branching molecule would treble the number of surface groups, etc. As the molecular weight and generation increases, the dendrimer tends to become more globular or spherical and the surface groups tend to become more closely packed. For a review of dendrimers their properties and applications see Klajnert et al. 2001, Vol. 48, 199-208.

Poly(amidoamine) (or PAMAM) dendrimers are one of the most well known types of dendrimers and are commercially available. The PAMAM dendrimers have branches comprised of branching amidoamine units ($-CH_2CH_2C(O)NHCH_2CH_2NH_2$) and are available with a variety of different cores and surface groups. The surface groups are the functional groups at the end of each branch of the dendrimer. In the case of PAMAM the surface group is usually an amino group. However, PAMAM dendrimers are available with alternative surface groups for example alcohol groups (commercially available and often referred to either PAMAM-OH or PAMAM-amidoethanol).

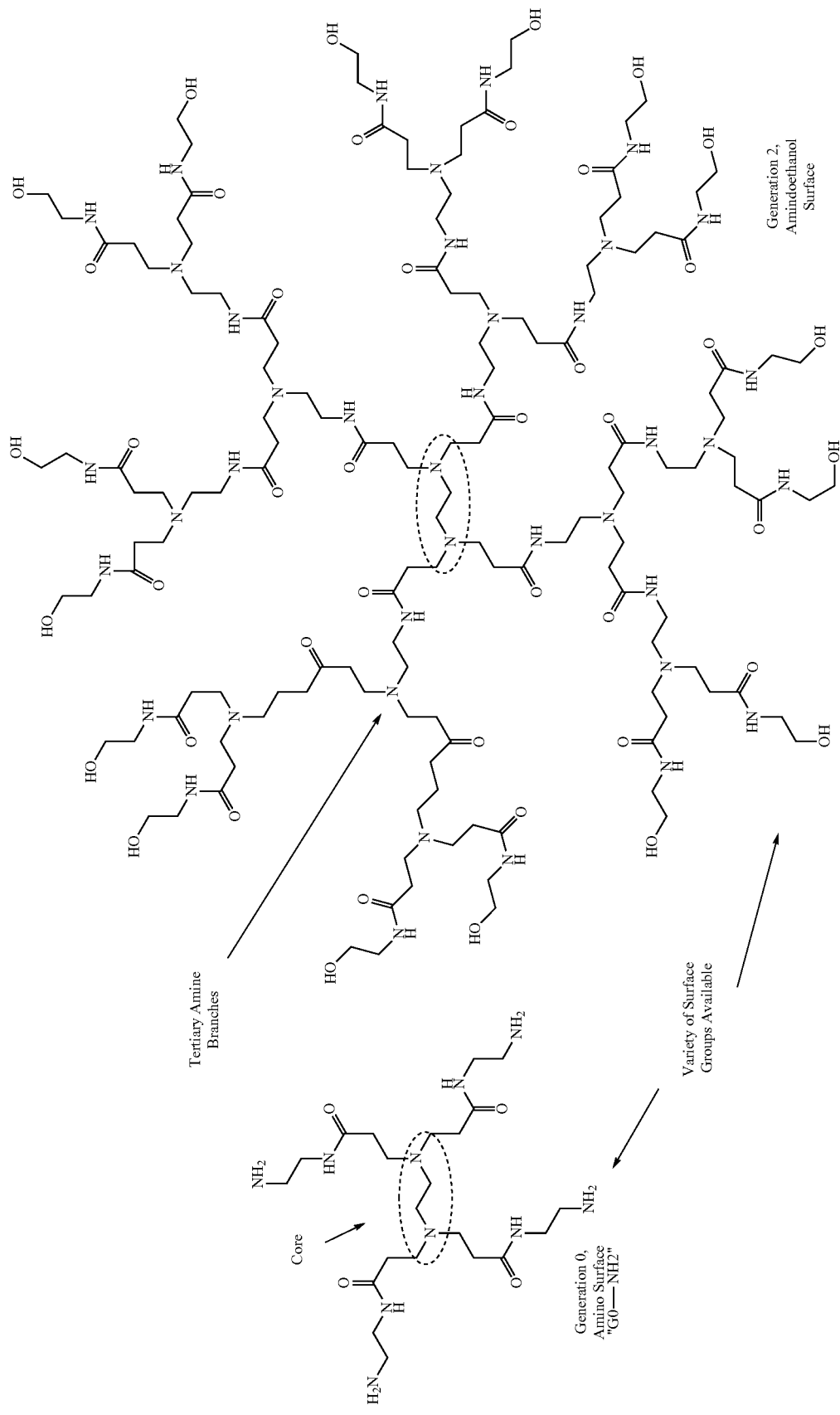

Other types of dendrimer include polyamine dendrimers (branches comprised of repeating amine units), polyimide dendrimers (branches comprised of repeating amide units), polypropyleneimine (PPI) dendrimers also known as polypropylamine (POPAM) dendrimers (branches comprised of repeating propylamine units), dendrimers based on poly (arylether) units and multiple antigen peptide (MAP) dendrimers which are based on repeating polylysine units.

A macromolecular scaffold may be decorated by conjugating ligands via the surface groups of the macromolecular scaffold. The number of ligands that can be conjugated onto a random polymer is relatively low compared to number of ligands which can potentially be conjugated to a well-defined highly branched macromolecular scaffold such as a dendrimer. Bioactive nanoparticles based on dendrimers therefore provide a means to achieve concentrated payloads of the active ligand.

In summary, dendrimers are particularly attractive scaffolds for the generation of bioactive nanoparticles for clinical applications because their size, structure and properties can be manipulated to suit its application and in particular because dendrimers can carry multiple ligands per molecule.

Unfortunately, the current approaches used to conjugate ligands onto random polymers are not powerful enough to enable more than partial ligand decoration of macromolecular scaffolds such as dendrimers. Problems occur from side reactions and incomplete reactions of the surface groups of the macromolecular scaffold which lead to structural defects. For clinical applications it is highly desirable to obtain a homogeneous and high degree of decoration, preferably fully decorated scaffolds, thereby maximizing the possible benefits to biological activity of multivalent display as well as ensuring homogeneity and reproducibility from batch to batch and within each batch.

Chemoselective ligations and bioconjugations are used to link complex or precious molecules and there are many different ligation techniques, including cycloadditions, the Staudinger ligation, olefin cross metathesis, native chemical ligation and hydrazone and oxime ligations. Attempts to apply some of these ligation techniques to dendrimers have been made. However, these techniques are generally not powerful enough to fully decorate dendrimers more complex than tetramers (i.e. a dendrimer with four surface groups) and octamers (i.e. a dendrimer with eight surface groups).

Oxime ligations (i.e. conjugation of two moieties via an oxime bond) have been used to conjugate biological molecules because the oxime bond is stable under physiological conditions. In particular, oxime bond forming condensation reactions between compounds bearing carbonyl groups and hydroxylamino nucleophiles have proven useful for the formation of a number of bioconjugates. However, the utility of these reactions in the formation of bioconjugates, and particularly in the formation of bioconjugates having multiple oxime bonds (i.e. polyoximes), has been hindered by the slow reaction rate at neutral pH.

Scheme 3 - An oxime-forming condensation reaction

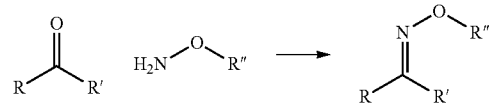

Rose et al. (*Bioconj. Chem.*, 1996, 7, 552-6) investigated conditions for the formation of oxime bonds between peptides and the stability of these bonds at various pH. In particular, Rose et al. studied oxime bond formation as a function of pH. In the case of single oxime bond formation, the condensation reaction was found to go essentially to completion at pH 3.0 and 4.6 but was markedly faster at lower pH. The reaction at pH 5.3 did not reach completion after 24 hours. In the case of polyoxime bond formation (i.e. formation of multiple oxime bonds on a single species), formation of the polyoxime product (a hexaoxime product in the investigation carried out by Rose et al.) was fastest at pH 2.1 and somewhat slower at pH 4.6. The oxime bond forming reaction did not take place at all at pH 7.0. Even at optimally low pH (i.e. 2.1), the major product was the penta- and not the hexaoxime, thus reflecting the limitations of the oxime bond forming reaction when applied to situations where multiple oxime bonds are being formed.

Dirksen and co-workers (see Dirksen et al. *Angewandte Chemie*, 2006, 45, 7581-7584) have investigated the oxime ligation between a glyoxylyl-functionalised peptide and an aminooxyacetyl-functionalised peptide and shown that the single oxime bond forming reaction can be catalysed using aniline at pH 4.5. The aniline catalyst was found to speed up the conjugation reaction rate but did not change the equilibrium position for the oxime ligation. Thus, the reactions investigated by Dirksen et al. eventually reached 99% conversion regardless of whether an aniline catalyst was employed or not.

Other efforts to improve the oxime ligation between functionalised peptides include utilising peptides functionalised with pyruvic acid in place of peptides functionalised with levulinic acid (see Kochendoerfer et al. *Bioconjugate Chem.*, 2002, Vol 13, 474-480). The pyruvic acid ketoxime bond is believed to be resonance-stabilized by conjugation with its carbonyl group and therefore it is thought that the oxime bonds formed in these ligations would be more stable than the related levulinic acid oxime.

Scheme 4 - oxime-forming reaction between a peptide functionalised with a pyruvic acid derivative and a peptide functionalised with aminooxyacetic acid derivative

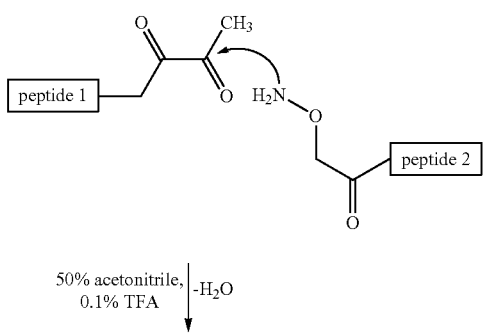

Ac-LYRAG = Ac-Leu-Tyr-Arg-Ala-Gly

Oxime ligations have also been applied in the formation of peptide and carbohydrate dendrimers (see Mitchell et al. *Bioorg Med Chem Lett.*, 1999, 2785-2788). However, as noted above while oxime ligation has proven to be useful in the formation of bioconjugates having a single oxime bond (for example in the formation of an oxime bond between two peptides), use of oxime ligation to decorate dendrimers (requiring the formation of multiple oxime bonds) with ligands has proved to be more challenging. Mitchell et al. found that even at G-1 PAMAM (a commercially available polyamidoamine dendrimer with eight amino surface groups) only partial decoration could be achieved. Various different reaction conditions were investigated by Mitchell et al. yet all attempts to fully decorate the dendrimer failed.

To date, one of the most successful methodologies for decorating dendrimers involves a native chemical ligation between a cysteine residue attached to the surface groups of a dendrimer and a peptide ligand prepared with a C-terminal thioester. Baal and co-workers (*Angew. Chem. Int. Ed*, 2005, 44, 5052-5057) reported successful decoration of G-2 PAMAM (i.e. a dendrimer with a valency of 16) using this method, although the batch of decorated dendrimer appeared to contain partially decorated products.

Scheme 5 - native chemical ligation between a cysteine residue attached to the surface groups of a dendrimer and a peptide ligand prepared with a C-terminal thioester

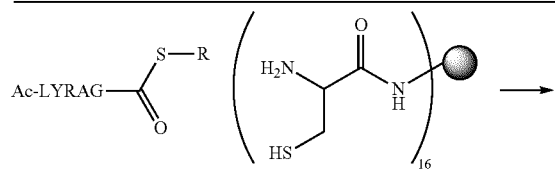

Another promising strategy which has been used for the preparation of decorated dendrimers employs "click chemistry". Specifically, reactions such as the azide-alkyne cycloadditions, have been investigated. Chun and co-workers utilised a copper-catalyzed cycloaddition reaction to conjugate peptides functionalised with azide groups to G-0 PAMAM dendrimers (i.e. a tetramer), modified with terminal alkyne groups (Australian Journal of Chemistry, 62, 1339-1342). A further example utilising "click chemistry" has been applied to a non-symmetrical dendrimer by Wu and co-workers (*Chem Commun.*, 2005, 5775-5777). Wu and co-workers achieved decoration of a scaffold with eight surface groups.

The decoration of dendrimer with more than eight surface groups still remains a challenge. Higher generation dendrimers are thought to adopt a conformation wherein the surface groups are shielded. For example, when there is a lack of binding interactions between both the dendrimer branches and the surface groups on dendrimers the dendrimer branches have high mobility and can fold inwards (see Boas et al. Dendrimers in medicine, 2006, 1-27). This back-folded conformation is believed to be more prevalent in higher generation dendrimers. Also, dendrimers (such as PAMAM and PPI dendrimers) which have basic surface groups as well as a basic interior are thought to be sensitive to pH. For example at low pH electrostatic repulsion between positively charged ammonium groups within the interior of dendrimers with amine containing branches are thought to result in an extended conformation (see Boas et al. Dendrimers in medicine, 2006, 1-27).

Scheme 6 - extended and back-folded conformations

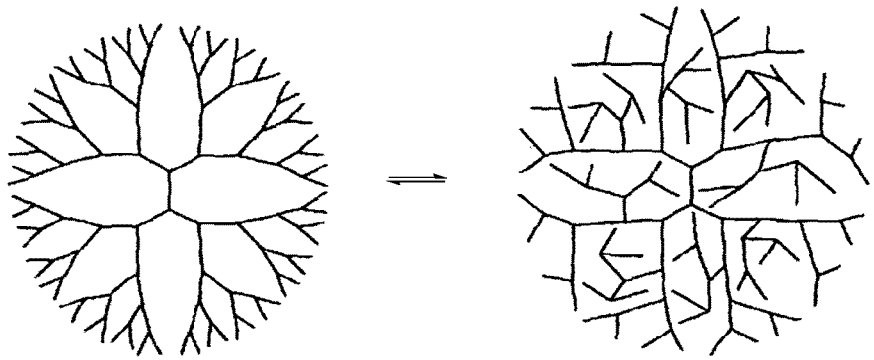

In summary, various ligation reactions have been employed in the conjugation of ligands to macromolecular scaffolds. Complete decoration of G-2 PAMAM has been reported using native ligation. However, the batch was not homogeneous. Only partial decoration of G-1 PAMAM has been achieved using oxime ligations and there remains a need to provide a method for generating highly decorated dendrimers, particularly those of higher generations. It is also desirable to provide a method which gives highly decorated dendrimers as a homogenous batch.

STATEMENT OF INVENTION

This invention provides a method for preparing a decorated macromolecular scaffold comprising the step of reacting the surface groups of a macromolecular scaffold with ligands to form oxime or hydrazone bonds between the surface groups of the macromolecular scaffold and the ligands, wherein the reaction is carried out in the presence of an aniline or substituted aniline catalyst.

BRIEF DESCRIPTION OF FIGURES

FIG. 4 shows rp-HPLC analysis of conjugation of AoA-EGSREQDWE with G2-(Pyr)$_{16}$ (A) and G3-(Pyr)$_{32}$ (B) after 20 h incubation under different reaction conditions as indicated; 1M sodium formate in 8 M urea, pH 3.0; 1M sodium acetate in 8 M urea, pH 4.6; and 1M sodium acetate, 0.1 M anilinium acetate in 8 NI urea, pH 4.6. The HPLC profiles show that the reaction goes almost to completion in the presence of aniline with a major shift of the peak corresponding to the peptide-dendrimer conjugate towards the right showing more extensive decoration.

DETAILED DESCRIPTION

Figure 1:
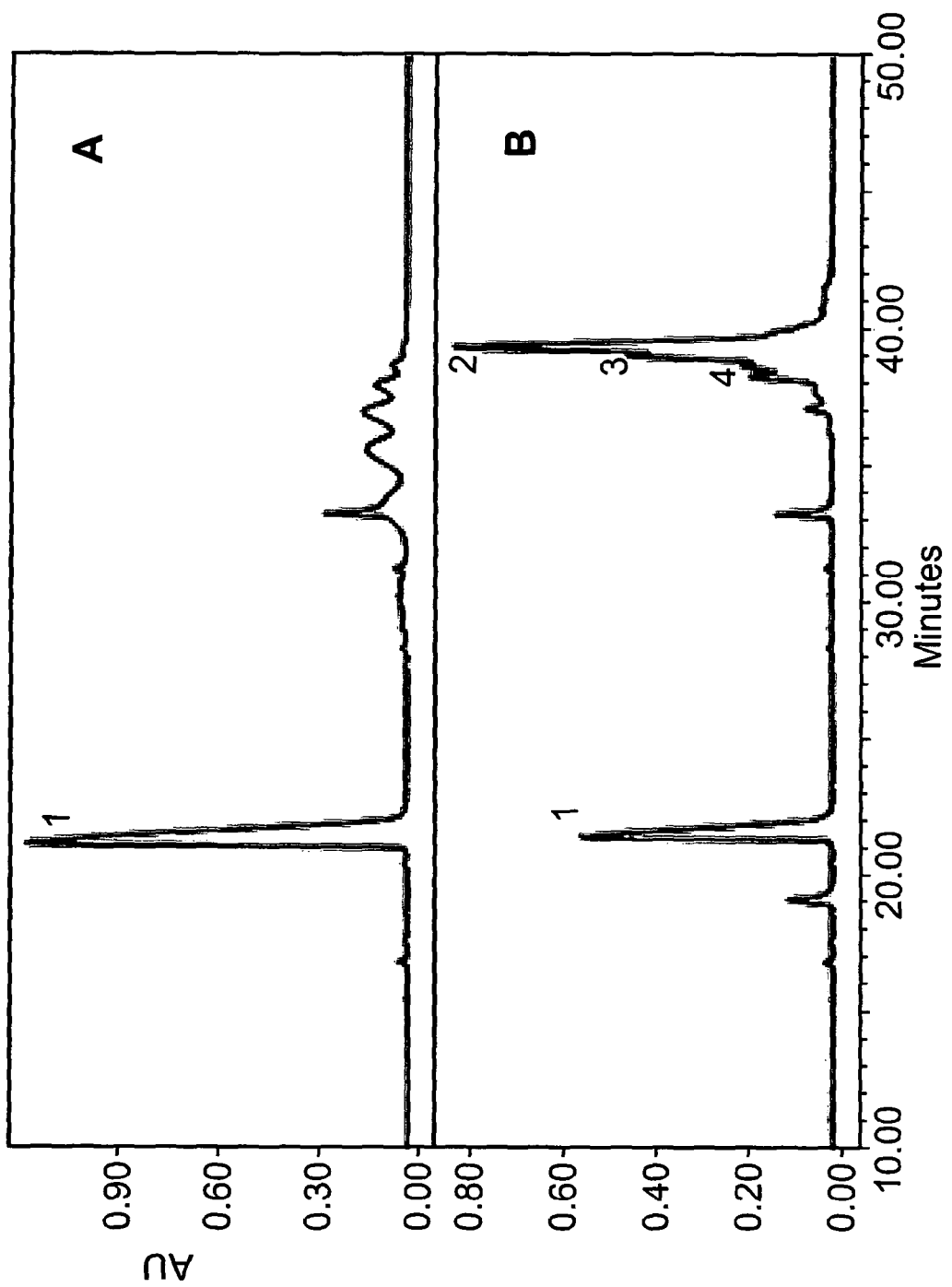
FIG. 1 shows the importance of aniline catalysis for full decoration of pyruvate-functionalised dendrimers by aminooxyacetyl-(AoA) functionalised peptides and proteins. Trace A and B are HPLC analyses of polyoxime formation after 15 h incubation at room temperature at pH 4.6, monitored at 214 nm. Reactions were carried out on 50 nmol G1-D(Pyr)$_8$ using 1.5 equivalents AoA-LYRAG per dendrimer Pyr-group (excess elutes at 21.5 min). Peak 1 corresponds to the excess of AoA-peptide, peak 2 to the target octaoxime. The octameric dendrimer starting material contains a hexameric dendrimer impurity, and peaks 3 and 4 correspond to products derived from these lower valency constructs (i.e. the fully decorated hexaoxime- and partially decorated pentaoxime). Traces of the incompletely decorated heptaoxime are also present. Trace A, reaction at pH 4.6; trace B, reaction at pH 4.6 in the presence of 0.1 M anilinium acetate.

This invention provides a method for preparing a decorated macromolecular scaffold comprising the step of reacting the surface groups of a macromolecular scaffold with ligands to form oxime or hydrazone bonds between the surface groups of the macromolecular scaffold and the ligands, wherein the reaction is carried out in the presence of an aniline or substituted aniline catalyst. A decorated macromolecular scaffold is obtained by conjugating a ligand to a surface group of the macromolecular scaffold. The present invention provides a method for preparing decorated macromolecular scaffolds which have a high degree of decoration and which have a high degree of homogeneity in the degree of decoration.

More particularly, the present invention provides a degree of decoration in which the mean number of decorated surface groups in each scaffold molecule is 50% or more, preferably 75% or more, preferably 80% or more, preferably 85% or more, preferably 90% or more, preferably 95% or more, more preferably 99%, even more preferably 100% of the available surface groups in each scaffold molecule.

The degree of decoration can be estimated by analytical HPLC for macromolecular scaffolds of up to approx 30 kDa. For larger constructs other approaches can be used, including SDS-PAGE and MALDI-TOF mass spectrometry. For macromolecular scaffolds of MW beyond 200 kDa other techniques such as ultra high resolution mass spectrometry (e.g. Fourier-Transform-Ion Cyclotron Resonance-Mass Spectrometry see Marshall A. G. Milestones in Fourier transform ion cyclotron resonance mass spectrometry technique development *International Journal of Mass Spectrometry* 200 (2000) 331-356) and/or sedimentation velocity analytical ultracentrifugation (see Schuck P. Size-Distribution Analysis of Macromolecules by Sedimentation Velocity Ultracentrifugation and Lamm Equation Modeling. *Biophysical Journal* 78, (2000), 1606-1619) could be employed to measure the degree of decoration.

The present invention also provides a degree of homogeneity in the degree of decoration in which 50% or more, preferably 60% or more, preferably 70% or more, preferably 80% or more, preferably 90% or more, preferably 95% or more, preferably 99% or more, preferably 100% of the decorated scaffold molecules have the modal number of decorations per scaffold molecule.

The method of the present invention comprises forming oxime or hydrazone bonds between the surface groups of the macromolecular scaffold and the ligands in the presence of an aniline or substituted aniline catalyst. Preferably, the method of the invention comprises the step of reacting the surface groups of a macromolecular scaffold with ligands to form oxime bonds between the surface groups of the macromolecular scaffold and the ligands, wherein the reaction is carried out in the presence of an aniline or substituted aniline catalyst.

An oxime bond is formed via an oxime bond forming condensation reaction between a carbonyl group and an aminooxy group. A hydrazone bond is formed via a hydrazone bond forming condensation reaction between a carbonyl group and a hydrazine or hydrazide group.

If the ligands and the surface groups of the macromolecular scaffold comprise functional groups capable of forming oxime or hydrazone bonds, direct reaction of the ligand and the surface groups of the macromolecular scaffold is possible. Typically, however, further functionalisation of the ligands and/or the surface groups of the macromolecular scaffold is necessary.

Suitable carbonyl (for example aldehyde or ketone functional groups), aminooxy, hydrazine or hydrazide functional groups can be introduced on the macromolecular scaffold by functionalising the surface groups of the macromolecular scaffold. Similarly, the carbonyl, aminooxy, hydrazine or hydrazide group can be introduced on the ligand by functionalising the ligand. Carbonyl refers to —C(O)—. An aminooxy group refers to —$ONH_2$. A hydrazine group refers to NH—$NH_2$. A hydrazide group refers to NH—$NH_2$ adjacent to an acyl (=O) group, for example —C(=O)NH—$NH_2$.

Preparing a Decorated Macromolecular Scaffold

In one embodiment, the method of the invention comprises the step of reacting the surface groups of a macromolecular scaffold, wherein the surface groups on the macromolecular scaffold comprise groups -$E^1$-$L^1$, with ligands wherein the ligands each comprise a group -$E^2$-$L^2$ to form an oxime or hydrazone bonds between the surface groups of the macromolecular scaffold and the ligands, wherein the reaction is carried out in the presence of an aniline or substituted aniline catalyst;
wherein $E^1$ and $E^2$ are independently each optional linkers;
wherein one of -$L^1$ or -$L^2$ is —C(O)—$Z^1$—C(O)$R^1$ and the other of -$L^1$ and -$L^2$ is —C(O)—$Z^2$—X—$NH_2$;
wherein $Z^1$ is selected from:
$(CH_2)_n$, or

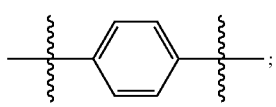

wherein $Z^2$ is selected from:
$(CH_2)_n$,

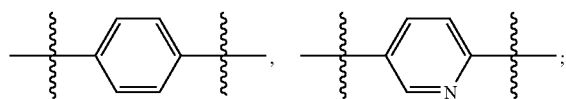

or —NH—NHC(O)—;
n is 0, 1, 2 or 3;
$R^1$ is H or $CH_3$; and
X is NH or O.

Scheme 7 - A schematic representation of the method of the invention

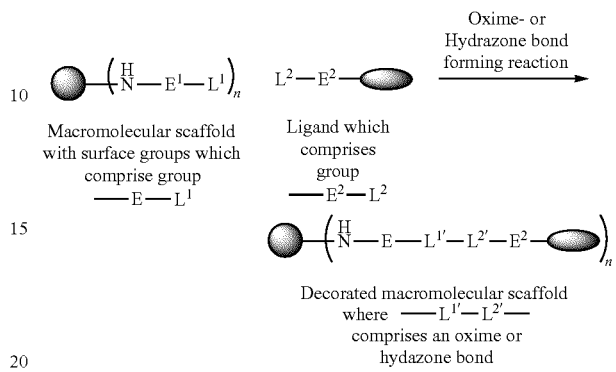

Optional Linkers $E^1$ and $E^2$

In one embodiment $E^1$ is an optional linker.

In a preferred embodiment the linker $E^1$ comprises a linear chain of up to 400 atoms, up to 700 atoms, up to 1000 atoms or up to 1300 atoms.

In a particularly preferred embodiment the linker $E^1$ comprises a linear chain of 10 to 100 atoms.

In one embodiment the linker $E^1$ comprises a PEG chain.

In one embodiment the linker $E^1$ comprises a PEG chain with between 1 and 30 ethylene oxide repeating units.

In a more preferred embodiment the linker $E^1$ is —C(O)—$(CH_2)_m$-PEG-NH—, wherein m is 0, 1, 2 or 3; and PEG is the repeating unit (—$OCH_2CH_2$—). Preferred $E^1$ linkers include —C(O)$CH_2OCH_2CH_2OCH_2CH_2NH$— and —C(O)$CH_2CH_2(OCH_2CH_2)_3NH$—.

In one embodiment $E^2$ is an optional linker. In a preferred embodiment $E^2$ is absent.

In a preferred embodiment the linker $E^2$ comprises a linear chain of 1 to 20 atoms, preferably 1 to 10 atoms, more preferably 1 to 5 atoms.

Preferably the linker $E^2$ is —NHCH($R^4$)—; wherein $R^4$ is $C_{1-6}$alkyl, $C_{2-6}$alkynyl, $C_{2-6}$alkenyl, $C_{3-10}$cycloalkyl, $C_{3-10}$heterocycloalkyl, $C_{6-10}$aryl, $C_{4-10}$heteroaryl, or the side chain of a naturally occurring amino acid. Preferably $R^4$ is $C_{1-6}$alkyl, or the side chain of a naturally occurring amino acid.

-$L^1$ and -$L^2$

-$L^1$ is —C(O)—$Z^1$—C(O)$R^1$ or —C(O)—$Z^2$—X—$NH_2$;
wherein $Z^1$ is selected from:
$(CH_2)_n$, or

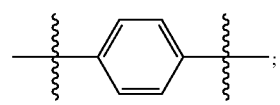

wherein $Z^2$ is selected from:
$(CH_2)_n$,

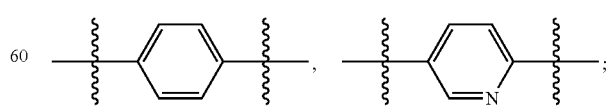

or —NH—NHC(O)—;
n is 0, 1, 2 or 3;
$R^1$ is H or $CH_3$; and
X is NH or O.

-$L^2$ is —C(O)—$Z^1$—C(O)$R^1$ or —C(O)—$Z^2$—X—$NH_2$;
wherein $Z^1$ is selected from:
$(CH_2)_n$, or

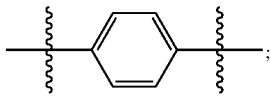

wherein $Z^2$ is selected from:
$(CH_2)_n$,

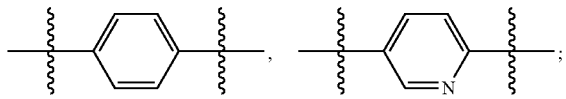

or —NH—NHC(O)—;
n is 0, 1, 2 or 3;
$R^1$ is H or $CH_3$; and
X is NH or O.

In one embodiment, one of -$L^1$ or -$L^2$ is —C(O)—$Z^1$—C(O)$R^1$;
wherein $Z^1$ is selected from:
$(CH_2)_n$, or

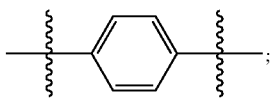 [SMILES: *c1ccc(*)cc1]

n is 0, 1, 2 or 3; and
$R^1$ is H or $CH_3$.

In one embodiment n is 0.

In another embodiment one of -$L^1$ or -$L^2$ is —C(O)—C(O)H, —C(O)—C(O)$CH_3$, —C(O)$CH_2CH_2$C(O)$CH_3$, or

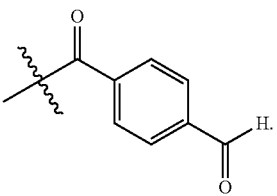

Preferably one of -L or -$L^2$ is —C(O)—C(O)$CH_3$.

In one embodiment, one of -$L^1$ and -$L^2$ is —C(O)—$Z^2$—X—$NH_2$;
wherein $Z^2$ is selected from:
$(CH_2)_n$,

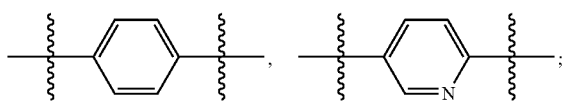

or —NH—NHC(O)—;
n is 0, 1, 2 or 3;
$R^1$ is H or $CH_3$; and
X is NH or O.

In another embodiment one of -$L^1$ or -$L^2$ is —C(O)—$CH_2$—O—$NH_2$,

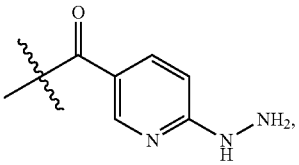

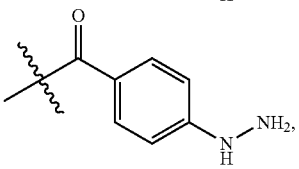

—C(O)—NH—$NH_2$, or —C(O)—NH—NH—C(O)—$NHNH_2$.

Preferably one of -$L^1$ or -$L^2$ is
—C(O)—$CH_2$—O—$NH_2$,

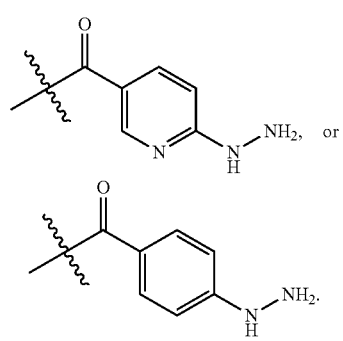

More preferably one of -$L^1$ or -$L^2$ is —C(O)—$CH_2$—O—$NH_2$.

-$L^1$-$L^2$-Bond

In one embodiment, -$L^1$ and -$L^2$ react to faint —C(O)—$Z^1$—C($R^1$)=N—X—$Z^2$—C(O)—.

In one embodiment, X is O and the groups -$L^1$ and -$L^2$ react to form an oxime bond.

In one embodiment, X is NH and the groups -$L^1$ and -$L^2$ react to form a hydrazone bond.

In a preferred embodiment, -$L^1$ is —C(O)C(O)$CH_3$ and -$L^2$ is —C(O)$CH_2$(O)$NH_2$ or -$L^2$ is C(O)C(O)$CH_3$ and -$L^1$ is —C(O)$CH_2$(O)$NH_2$. In a particularly preferred embodiment, -$L^1$ is —C(O)C(O)$CH_3$ and -$L^2$ is —C(O)$CH_2$(O)$NH_2$.

Macromolecular Scaffold

In one embodiment, the macromolecular scaffold is a dendrimer or a dendron. Preferably the macromolecular scaffold is a dendrimer, more preferably a PAMAM dendrimer (poly (amidoamine) dendrimer), more preferably a PAMAM dendrimer comprising amino surface groups.

In another embodiment the macromolecular scaffold comprises amino, aldehyde (such as carboxybenzaldehyde), alcohol (such as —$NHCH_2CH_2OH$) or N-(2-Hydroxydodecyl) surface groups or combinations of the above.

Examples of dendrimers comprising aldehyde surface groups include phosphorus dendrimers with a thiophosphoryl chloride core and 3, 6, 12, 24, 48 or 96 carboxybenzaldehyde surface groups and phosphorus dendrimers with a hexachlorocyclotriphosphazene core and 6, 12, 24, 48 or 96 carboxybenzaldehyde surface groups. These dendrimers are examples of macromolecular scaffolds which can be used directly in the method of the invention, i.e. the surface groups do not require functionalisation.

In one embodiment the macromolecular scaffold comprises amino surface groups. These surface groups may be functionalised to form a macromolecular scaffold having surface groups which comprise groups -$E^1$-$L^1$.

In a more preferred embodiment the macromolecular scaffold is a dendrimer comprising amino surface groups which is functionalised to form a macromolecular scaffold having surface groups which comprise -$E^1$-$L^1$.

Dendrimers comprising amino surface groups include PAMAM dendrimers (poly(amidoamine) dendrimers) with an ethylenediamine, 1,4-diaminobutane, 1,6-diaminohexane or cystamine central core. However, any dendrimer comprising amino surface groups can be used as the macromolecular scaffold in the method of the invention. Examples of other types of dendrimers comprising amino surface groups which can be used as macromolecular scaffolds include dendrimers based on polyamines, polyamides, polypeptides i.e. peptide dendrimers (see Sadler K and Tam J P, Reviews in Molecular Biotechnology 90, 2002.195-229), polypropyleneimines, and those built up by poly(aryl ether) subunits.

The macromolecular scaffold may comprise more than one type of surface group. In a preferred embodiment all surface groups on the macromolecular scaffold are the same.

In one embodiment, the macromolecular scaffold comprises more than one type of surface group. Preferably one of the types of surface groups are amino surface groups. Examples of macromolecular scaffolds which comprise more than one type of surface group include PAMAM dendrimers with amino and N-(2-Hydroxydodecyl) surface groups and PAMAM dendrimers with amino and alcohol surface groups.

The amino surface groups of a macromolecular scaffold which comprises more than one type of surface group may be functionalised with -$E^1$-$L^1$ and reacted with ligands each comprising -$E^2$-$L^2$ to form an oxime or hydrazone bond. The other type of surface group which is present on a macromolecular scaffold which comprises more than one type of surface group is typically not functionalised with -$E^1$-$L^1$ and therefore does not react with ligands comprising an -$E^2$-$L^2$ group. The surface group which does not comprise -$E^1$-$L^1$ is therefore free to participate in some other bond forming reaction or type of conjugation reaction.

The method of the invention may also be applied to dendrons, for example half dendrimers, for the generation of decorated heterodendrimers. This approach allows one type of ligand to be introduced on one dendron (e.g. one half of a dendrimer) and a different type of ligand to be introduced on another dendron (e.g. the second half of a dendrimer). The different dendrons can then be joined together to form a decorated heterodendrimer carrying two or more different types of ligands (for example a targeting moiety, a drug payload and/or a fluorescent tracer).

In an alternative embodiment, dendrons comprising different surface groups may be joined together and the different dendrons then functionalised and/or reacted with different ligands chemoselectively to form a decorated heterodendrimer.

The central core of the PAMAM dendrimer is preferably ethylenediamine, 1,4-diaminobutane or cystamine.

A dendrimer with a cystamine core can be divided into dendrons by opening the cystamine core. The resulting sulfhydryl-bearing dendrons can be decorated separately and then re-coupled together to give a dendrimer with a cystamine central core.

Preferably, the central core of the PAMAM dendrimer is cystamine when the method of the invention is applied to decorate a heterodendrimer.

The PAMAM dendrimer is preferably generation 0 (GM) generation 1 (G-1), generation 2 (G-2), generation 3 (G-3), generation 4 (G-4), generation 5 (G-5), generation 6 (G-6), or generation 7 (G-7). More preferably, the PAMAM dendrimer is generation 0 (GM) generation 1 (G-1), generation 2 (G-2), generation 3 (G-3), or generation 4 (G-4). More preferably the PAMAM dendrimer is generation 2 (G-2), or generation 3 (G-3).

Ligands

The ligand may be a peptide, protein, glycopeptides, carbohydrates, oligonucleotides, antigen, biological targeting reagent (for example antibody or fragments thereof), biological effectors (for example toxins, receptor agonist), drug, vaccine or florescent tracer.

The method of the invention is particularly useful for decorating macromolecular scaffolds with large ligands.

In one embodiment a large ligand is a ligand with a molecular weight of 500 Daltons or higher, preferably 1000 Daltons or higher, more preferably 2000 Daltons or higher, or even more preferably 3000 Daltons or higher.

In a preferred embodiment the ligand is a peptide or protein.

When the ligand is a peptide or a protein, a large ligand is a peptide or a protein with 5 or more, preferably 10 or more, more preferably 15 or more, even more preferably 20 or more, even more preferably 25 or more, most preferably 30 or more amino acid residues.

More preferably the ligand is a peptide.

Aniline or Substituted Aniline Catalyst

The oxime or hydrazone bond forming reaction of the invention is carried out in the presence of aniline or substituted aniline. The aniline or substituted aniline acts as a catalyst in the oxime or hydrazone bond forming condensation reaction.

As mentioned in the background section, the oxime or hydrazone bond forming reaction is sensitive to pH. According to the prior art, even at optimally low pH, the oxime or hydrazone bond forming reaction does not go to completion when there are multiple oxime or hydrazone bonds being formed. Using the method of the invention, carried out in the presence of an aniline catalyst, highly decorated macromolecular scaffolds can be obtained. Furthermore, by using an aniline catalyst the oxime or hydrazone bond forming reaction can be carried out at milder pH, typically between pH 3.0 and 7.0, preferably between 4.0 to 6.0, more preferably between pH 4.0 to 5.5, even more preferably between pH 4.2 to 4.8, most preferably at pH 4.6.

Decoration of macromolecular scaffolds having a valency of greater than eight is difficult to achieve without the use of a catalyst. The method of the invention is particularly useful for decorating macromolecular scaffolds with more than eight surface groups.

In one embodiment the macromolecular scaffold has a valency of greater than 4, preferably greater than 8, more preferably greater than 16.

In another embodiment the macromolecular scaffold is a dendrimer having a generation 0 (G-0) or higher, preferably 1 (G-1) or higher, more preferably 2 (G-2) or higher.

The ability of aniline or unsubstituted aniline to function as a catalyst in the oxime- or hydrazone-bond forming condensation reaction is based on the property of aniline or substituted aniline to react with protonated carbonyl groups to form imines. The pKa of these aniline imines is such that they are significantly protonated at the pH of the reaction mixture.

Without wishing to limit the scope of the present invention, it is believed that under the reaction conditions the aniline is protonated to form a protonated aniline Schiff base which is a highly reactive electrophile. The electrophile reacts rapidly with an aminooxy or hydrazine reagent, forming an oxime or hydrazone product that does not readily re-react with aniline. The ability to generate a reactive species without competing with the desired product is a key property of any nucleophilic catalyst.

Scheme 8 - aniline as a catayst in oxime-bond forming condensation reaction

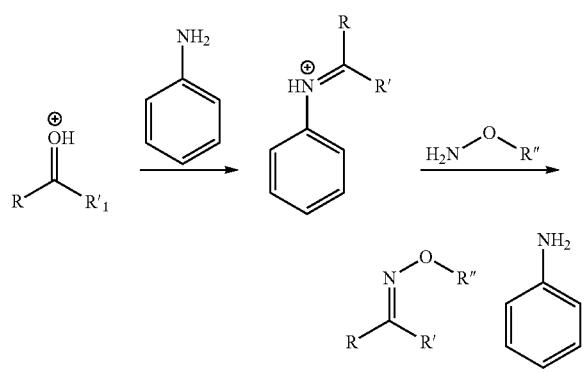

Aniline has a pKa of 4.6. Preferably, substituted aniline employed in the present invention are selected from substituted aniline having a pKa of 4.0 or higher. In a preferred embodiment the aniline or substituted aniline is aniline. Aniline is a mild, fairly unreactive nucleophile and is therefore compatible with many functional groups and ligands including unprotected peptides. Furthermore, aniline is soluble in a range of solvents and can be used as a convenient aqueous buffer with acetic acid and both its solubility and nucleophilicity can be tuned through the introduction of substituents on the aromatic ring.

pKa of monosubstituted aniline derivatives:

TABLE 1 pKa values for monosubstituted aniline derivatives

| Substituent | o- | m- | p- |
|---|---|---|---|
| H— | 4.6 | 4.64 | 4.58 |
| $CH_3O_2C$— | 2.16 | 3.56 | 2.30 |
| $CH_3S$— | 4.05 | 4.40 | — |
| Br— | 2.6 | 3.51 | 3.91 |
| F— | 2.96 | 3.38 | 4.52 |
| $CH_3O$— | 4.49 | 4.20 | 5.29 |
| $C_6H_5$— | 3.78 | 4.18 | 4.27 |
| $(CH_3)_3C$— | 3.78 | | |
| $O_3S$— | 3.80 | 3.32 | 3.78 |
| $O_2N$— | −0.28 | 2.45 | 0.98 |
| $HO_2C$— | 2.04 | 3.05 | 2.32 |
| $C_2H_5O_2C$— | 2.10 | 2.38 | — |
| $F_3C$— | 3.49 | 2.57 | — |
| HO— | 4.72 | 4.17 | 5.50 |
| Cl— | 2.62 | 3.32 | 3.81 |
| $C_2H_5O$— | 4.47 | 4.17 | 5.25 |
| $CH_3$— | 4.38 | 4.67 | 5.07 |
| $H_2N$— | 4.47 | 4.88 | 6.08 |

Preferred aniline catalysts include:

TABLE 2

Preferred aniline catalysts

| Compound | substitution | pKa |
|---|---|---|
| p-methoxyaniline | —O—$CH_3$ | 5.3 |
| p-toluidine | —$CH_3$ | 5.1 |
| 4-ethoxy aniline | —O—$C_2H_5$ | 5.2 |
| Aniline | —H | 4.6 |

General Conjugation Conditions

The oxime or hydrazone bond forming condensation reaction is performed in the presence of an aniline or substituted aniline, with the ligand in excess over each surface group present on the macromolecular scaffold.

In one embodiment the oxime or hydrazone bond forming condensation reaction is performed at a pH range of from 3.0 to 7.0. Preferably the oxime or hydrazone bond forming condensation reaction is performed at a pH range of from 4.0 to 5.5. More preferably the oxime or hydrazone bond forming condensation reaction is performed at pH 4.6.

In one embodiment, the aniline or substituted aniline is present in the oxime or hydrazone bond forming condensation reaction at a concentration in the range of from 10 mM to 0.2M. Preferably the aniline or substituted aniline is present in the oxime or hydrazone bond forming condensation reaction at 0.1M.

The aniline or substituted aniline is present in the oxime or hydrazone bond forming condensation reaction in an amount 20 to 100-fold excess, preferably 50-fold excess, with respect to the number of moles of surface groups.

In one embodiment, the ligand is present in the oxime or hydrazone bond forming condensation reaction in from 1.1 to 5.0-fold excess over each surface group present. Preferably, the ligand is present in the oxime or hydrazone bond forming condensation reaction in from 1.5 to 3.0-fold excess. More preferably, the ligand is present in the oxime or hydrazone bond forming condensation reaction at 2.0-fold excess.

Elongation of Macromolecular Scaffold or Ligand

Optionally, the branches of the macromolecular scaffold may be elongated. In one embodiment, the macromolecular scaffold is reacted to introduce a linker $E^1$. The linker $E^1$ acts as a spacer arm. The resulting elongated macromolecular scaffold can then be reacted to introduce -$L^1$.

The macromolecular scaffold which comprises an optional linker may be reacted to introduce the group -$L^1$.

Scheme 9 - Forming a macromolecular scaffold with surface groups which comprise groups ——$E^1$—$L^1$

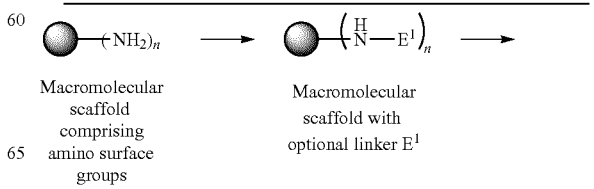

Macromolecular scaffold comprising amino surface groups

Macromolecular scaffold with optional linker $E^1$

-continued

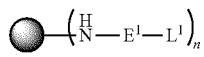

Macromolecular
scaffold with
surface groups which
comprise group
—$E^1$—$L^1$

In an alternative embodiment the macromolecular scaffold may be reacted to introduce the group -$E^1$-$L^1$ in a single step.

In one embodiment, the linker $E^1$ is attached to the macromolecular scaffold by activating a Boc-amino-PEG-COOH chain by esterification and subsequently reacting the activated linker with the macromolecular scaffold. Preferably, the Boc-amino-PEG-COOH chain is activated by esterification with pentafluorophenol to yield Boc-amino-PEG-pentafluorophenyl ester.

Preferred Boc-amino-PEG-COOH chains are Boc-ATOPA and Boc-AEEA.

Preferably a macromolecular scaffold comprising linker $E^1$ is prepared by reacting the macromolecular scaffold with Boc-amino-PEG-pentafluorophenyl ester and subsequently deprotecting the terminal amino functional group.

When the amino group on the PEG chain comprises a nitrogen protecting group, the nitrogen protecting group is removed to reveal an amino group. The resulting macromolecular scaffold comprising linker $E^1$, wherein $E^1$ comprises amino groups, can be functionalised in the same manner as any macromolecular scaffold comprising amino surface groups.

In one embodiment the ligands are each reacted to introduce a linker $E^2$.

In an alternative embodiment the ligand may be reacted to introduce the group -$E^2$-$L^2$ in a single step.

Macromolecular Scaffolds with Surface Groups which Comprise Groups -$E^1$-$L^1$

When the surface group of the macromolecular scaffold does not comprise a group -$E^1$-$L^1$ which can participate in an oxime or hydrazone bond forming condensation reaction, the surface groups of the macromolecular scaffold may be reacted to introduce the group -$E^1$-$L^1$.

In one embodiment, the method of the invention further comprises the step of reacting a macromolecular scaffold to introduce groups -$E^1$-$L^1$.

Preferably, the surface groups on the macromolecular scaffold, which are reacted with ligands, comprise groups -$E^1$-$L^1$.

The macromolecular scaffold having surface groups which comprise groups -$E^1$-$L^1$ can be formed by reacting the surface groups of the macromolecular scaffold using standard chemical procedures known to the skilled person.

Ligands which Comprise Group -$L^2$

When the ligands do not comprise group -$E^2$-$L^2$ which can participate in an oxime or hydrazone bond forming condensation reaction, the ligand may be reacted to introducing a group -$E^2$-$L^2$.

In one embodiment, the method of the invention further comprises the step of reacting ligands to introduce group -$E^2$-$L^2$.

Preferably, the ligands which are reacted with the macromolecular scaffold comprise a group -$E^2$-$L^2$.

The ligand which comprises group -$E^2$-$L^2$ group can be formed by site specifically modifying a ligand using standard chemical procedures known to the skilled person.

Forming a Macromolecular Scaffold with Surface Groups which Comprise Groups -$E^1$-$L^1$ Preferably the macromolecular scaffold with surface groups which comprise groups -$L^1$ are prepared from a macromolecular scaffold which comprises amino surface groups.

When an optional linker $E^1$ is present, the macromolecular scaffold with surface groups which comprise groups -$E^1$-$L^1$ are preferably prepared from a macromolecular scaffold which comprises group -$E^1$, wherein group -$E^1$ comprises an amino group.

When -$L^1$ is —C(O)—$Z^1$—C(O)$R^1$, the macromolecular scaffold with surface groups which comprise groups -$L^1$ can be prepared by reacting the macromolecular scaffold with $L^1$-$R^2$, wherein $R^2$ is:

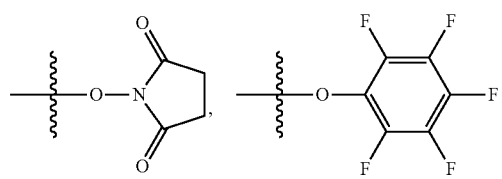 [SMILES: *ON1C(=O)CCC1=O ; *Oc1c(F)c(F)c(F)c(F)c1F]

or O—$R^5$; such that $L^1$-$OR^5$ is an anhydride ($R^5$ is $L^1$) or mixed anhydride ($R^5 \neq L^1$)

Preferably $R^2$ is

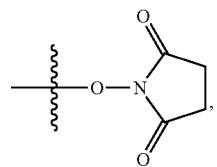 [SMILES: *ON1C(=O)CCC1=O]

Preferably $L^1$-$R^2$ is:

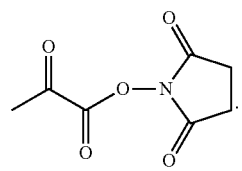

When -$L^1$ is —C(O)—$Z^2$—X—$NH_2$, the macromolecular scaffold with surface groups which comprise groups -$E^1$-$L^1$ can be prepared by
(i) reacting the macromolecular scaffold with $L^3$-$R^3$, wherein -$L^3$ is —C(O)—$Z^2$—X—$NP^1P^2$;
wherein, $Z^2$ and X are as defined for -$L^1$;
Wherein $P^1$ and $P^2$ are selected from H and nitrogen protecting groups, wherein $P^1$ and $P^2$ may combine to form a nitrogen protecting group, provided at least one of $P^1$ and $P^2$ is a nitrogen protecting group;
and wherein $R^3$ is

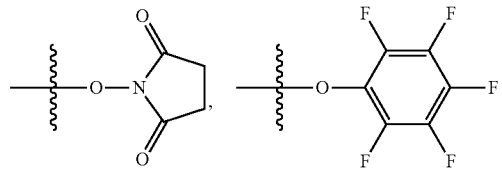 [SMILES: *ON1C(=O)CCC1=O ; *Oc1c(F)c(F)c(F)c(F)c1F]

or $OR^5$; such that $L^3$-$OR^5$ is an anhydride ($R^5$ is $L^3$) or mixed anhydride ($R^5 \neq L^3$); and
(ii) subsequently deprotecting —$NP^1P^2$.

Preferably, —NP¹P² is selected from the following groups

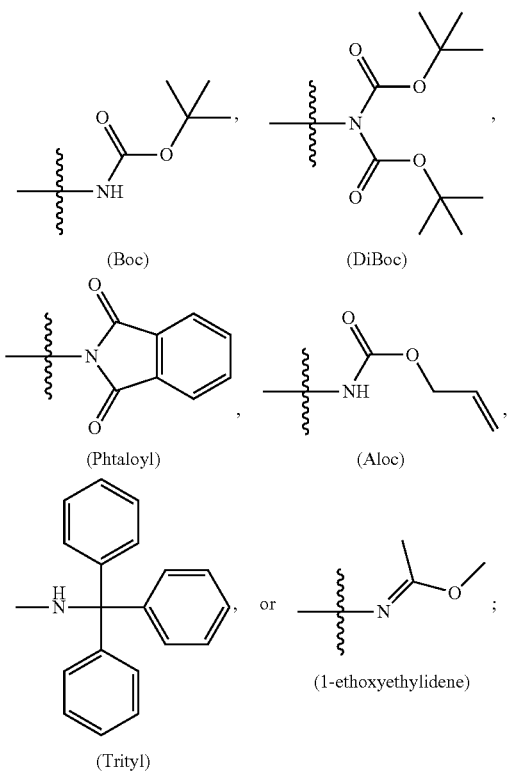

(Boc) (DiBoc)
(Phtaloyl) (Aloc)
(Trityl) (1-ethoxyethylidene)

Preferably R³ is

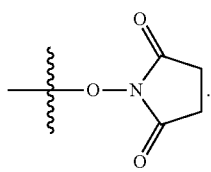

Preferably L³-R³ is

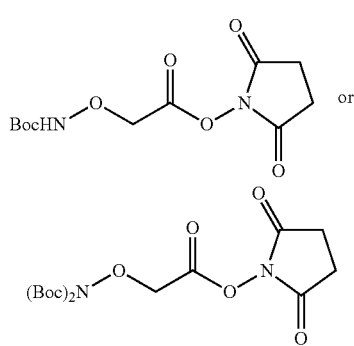

Deprotection of the —NP¹P² group after reacting L³-R³ with the macromolecular scaffold provides a macromolecular scaffold having surface groups which comprise -E¹-L¹, wherein -E¹-L¹ is —C(O)—Z²—X—NH₂.

Alternatively, the surface groups of the macromolecular scaffold may already comprise group -E¹-L¹ and the additional step of forming a macromolecular scaffold with surface groups which comprise -E¹-L¹ is not required. A macromolecular scaffold having carboxybenzaldehyde surface groups is an example of a macromolecular scaffold which has surface groups which comprises group -E¹-L¹, which may participate in an oxime-bond forming condensation reaction. Aromatic aldehydes such as benzaldehyde are potent electrophiles and are more reactive than ketones and glyoxylyl (—C(O)CHO) groups typically used in oxime- or hydrazine-bond forming condensation reactions, but they can dramatically reduce the water solubility of the dendrimer scaffold.

An alternative method of preparing a macromolecular scaffold with surface groups which comprise -E¹-L¹ involves introducing N-terminal serine or threonine residues on the macromolecular scaffold and oxidising the residue with NaIO₄. A similar method for preparing a macromolecular scaffold with surface groups which comprise -E¹-L¹ involves introducing N-terminal alanine and transforming the residue into an —NHCOCHO group by oxidative transamination using glyoxylic acid/Cu⁺.

A further method for preparing a macromolecular scaffold with surface groups which comprises an aldehyde involves incorporating an amino acid with a masked aldehyde. The masked aldehyde acts as a precursor to an aldehyde group which can participate in an oxime or hydrazone bond forming condensation reaction. An example of an amino acid with a masked aldehyde is L-2-amino-4,5-dihydroxy-pentanoic acid (see Spetzler, J. C., and Hoeg-Jensen, T. (2001) *J. Pept. Sci.* 7, 537-551).

In a preferred embodiment, the macromolecular scaffold is a PAMAM dendrimer comprising amino surface groups. A macromolecular scaffold with surface groups which comprise -E¹-L¹ is formed by reacting the macromolecular scaffold with L¹-R²; wherein L¹-R² is

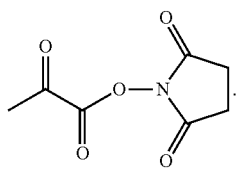

Forming Ligands which Comprise Groups -L²

Ligands which each comprise group -E²-L² can be prepared from ligands comprising amino groups.

When the ligand is a peptide, the ligands which each comprise group -E²-L² can be formed by site-specifically modifying the ligands with -E²-L² at either the N-terminus or at the C-terminus. The E²-L² group can be attached to an amino group at the N-terminus of the peptide. Alternatively, the E²-L² group can be attached to the C-terminal residue via an amino group on the residue side chain (for example via the epsilon amine of a lysine residue).

Similarly, when the ligand is a protein, the ligands which each comprise group -E²-L² can be formed by site-specifically modifying the ligands with -E²-L² at either the N-terminus or at the C-terminus. The E²-L² group can be attached to an amino group at the N-terminus of the protein. Alternatively, the E²-L² group can be attached to the C-terminal residue by introduction of a supplementary cysteine residue for further functionalisation with -E²-L². In the same way that cysteine variants are produced by mutagenesis for site specific PEGylation of proteins (see for example Doherty D H, Rosendahl M S, Smith D J, Hughes J M, Chlipala E A, Cox G N Site-specific PEGylation of engineered cysteine analogues of recombinant human granulocyte-macrophage colony-stimulating factor *Bioconjug Chem.* 2005; 16, 1291-8), the thiol on the engineered cysteine can be used to introduce the appropriate functionality using an heterobifunctional linker such as $L^2$-NH(CH$_2$)$_2$—NH—CO(CH$_2$)$_2$—N-maleimide.

When $L^2$ is —C(O)—Z$^1$—C(O)R$^1$, the ligands which each comprise groups -E$^2$-L$^2$ can be prepared by reacting the ligands with L$^2$-R$^2$ wherein R$^2$ is

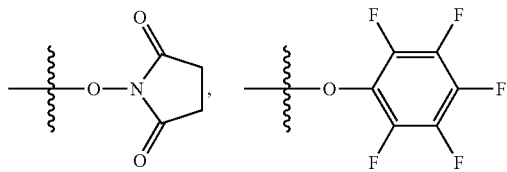

or OR$^5$; such that L$^2$-OR$^5$ is an anhydride (R$^5$ is L$^2$) or mixed anhydride (R$^5$≠L$^2$).

Preferably R$^2$ is

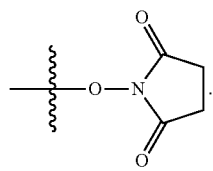

Preferably L$^2$-R$^2$ is

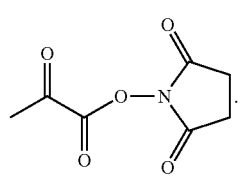

When $L^2$ is —C(O)—Z$^2$—X—NH$_2$, the ligand which each comprise groups -L$^2$ can be prepared by
(i) reacting the ligands with L$^3$-R$^3$,
wherein -L$^3$ is —C(O)—Z$^2$—X—NP$^1$P$^2$;
wherein Z$^2$ and X are as defined for -L$^2$; and
wherein P$^1$ and P$^2$ are selected from H and nitrogen protecting groups, wherein P$^1$ and P$^2$ may combine to form a nitrogen protecting group, provided at least one of P$^1$ and P$^2$ is a nitrogen protecting group;
and wherein R$^3$ is

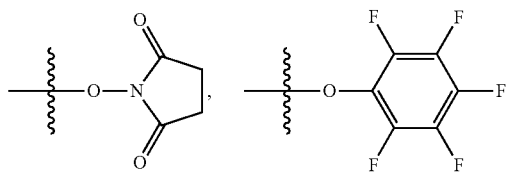 [SMILES: *ON1C(=O)CCC1=O ; *Oc1c(F)c(F)c(F)c(F)c1F]

or OR$^5$; such that L$^3$-OR$^5$ is an anhydride (R$^5$ is L$^3$) or mixed anhydride (R$^5$≠L$^3$)$^2$; and
(ii) and subsequently deprotecting —NP$^1$P$^2$.

Preferably, NP$^1$P$^2$ is selected from the following groups

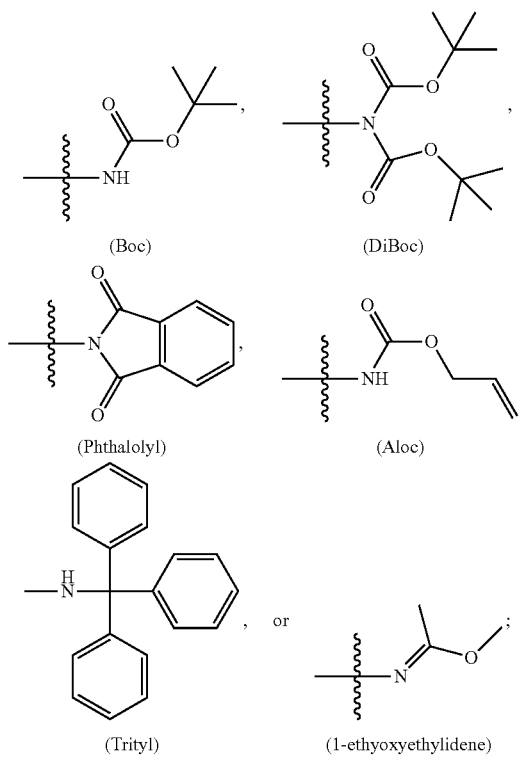

Preferably R$^3$ is

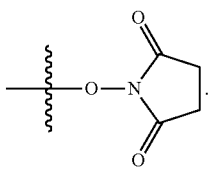 [SMILES: *ON1C(=O)CCC1=O]

Preferably L$^3$-R$^3$ is

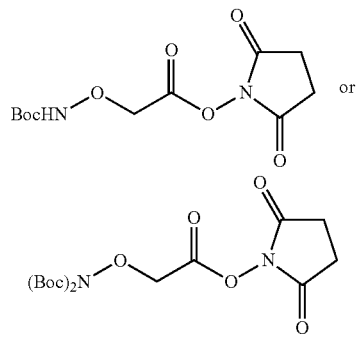

Deprotection of the —NP$^1$P$^2$ group after reacting L$^3$-R$^3$ with the ligands provides ligands which each comprise -E$^2$-L$^2$, wherein -L$^2$ is —C(O)—Z$^2$—X—NH$_2$.

Alternatively, ligands which each comprise group -E$^2$-L$^2$ can be formed by site specifically modifying the ligand with by oxidising appropriate terminal residues. For example, when the ligand has a N-terminal serine, theonine or alanine, these groups can be transformed into -E²-L² wherein -E²-L² is —NHCOCHO group by oxidation with NaIO₄. When the ligand has a N-terminal alanine the terminal group can be transformed into -E²-L² wherein -L² is —NHCOCHO by oxidative transamination using glyoxylic acid/Cu⁺.

In a preferred embodiment, the ligand is a peptide or protein. The ligands which each comprise group -E²-L² are prepared by site specifically modifying the ligand by
(i) reacting an amino group at the N-terminus of the peptide or protein with L³-R³;
wherein L³-R³ is

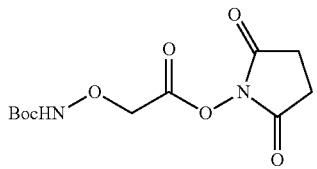 [SMILES: CC(C)(C)OC(=O)NOCC(=O)ON1C(=O)CCC1=O]

and
(ii) subsequently deprotecting the nitrogen.

Certain features of the invention, which are described in the context of separate embodiments, can also be combined.

Definitions

"Decorated macromolecular scaffold" refers to a macromolecular scaffold which has ligands conjugated to its surface groups.

"Dendrimer" refers to a branched macromolecular scaffold synthesised in a stepwise manner from a central core to generate a molecule comprising surface group.

"Heterodendrimer" refers to a dendrimer with two or more different types of surface groups.

"Decorated heterodendrimer" refers to a dendrimer with two or more different types of ligands conjugated to its surface groups.

"Surface groups" refers to functional groups on the surface of the macromolecular scaffold. More particularly "surface groups" refers to functional groups on the terminal end of the branches stemming from a central core.

"The side chain of a naturally occurring amino acid" refers to the R group of a natural occurring amino acid with the general structure $NH_2$—CH(R)—COOH. Naturally occurring amino acids are glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, and glutamine.

"amino" refers to $NH_2$

"α-amido aldehyde" refers to —NHC(O)COH

"α-amido ketone" refers to —NHC(O)C(O)R. R is $C_{1-6}$ alkyl, preferably $CH_3$.

"Oxime ligation" refers to an oxime bond forming condensation reaction between a carbonyl group and an aminooxy group.

"Hydrazone ligation" refers to a hydrazone bond forming condensation reaction between a carbonyl group and a hydrazine or hydrazide group.

"Spacer arm" refers to a linker E which can be tagged onto the surface group of a dendrimer to extend the branch.

"Terminal group" refers to a functional group at the end of a molecule or branch.

"PEG" refers to polyethyleneglycol.

"Boc-AEEA" refers to 2-[2-(Boc-amino)ethoxy]ethoxy)acetic acid.

"Boc-ATOPA" refers to Boc-15-amino-4,7,10,13-tetraoxapentanedecanoic acid.

"AEEA" refers to —$C(O)CH_2OCH_2CH_2O\ CH_2CH_2NH$—

"ATOPA" refers to —$C(O)CH_2OCH_2CH_2O\ CH_2CH_2NH$—

"AoA" refers to aminooxyacetyl or —$C(O)CH_2ONH_2$

"ESI" refers to electrospray ionisation

"MALDI" refers to Matrix assisted laser desorption ionisation

"TOF" refers to time of flight

"MS" refers mass spectrometry

"SDS-PAGE" refers to sodium dodecyl sulfate polyacrylamide gel electrophoresis

"MVHA49-72" refers to the measles virus haemagluttenin-derived peptide Leu-Ile-Gly-Leu-Ala-Ile-Ala-Gly-Ile-Arg-Leu-His-Arg-Ala-Ala-Ile-tyr-Thr-Ala-glu-Ile-His-Lys "LYRAG" refers to Leu-Tyr-Arg-Ala-Gly "Pfp" refers to pentafluorophenyl "Su" refers to succinimide "Pyr" refers to $CH_3COC(O)$—

"Pyr=AoA" refers to —$C(O)C(CH_3)$═N—O—$CH_2$—C(O)—.

"AEEA-Pyr=AoA" refers to —$C(O)CH_2OCH_2CH_2OCH_2CH_2NH$—$C(O)C(CH_3)$═N—O—$CH_2$—C(O)—

"G-1(AEEA-Pyr=AoA-Insulin)$_8$" refers to a generation 1 dendrimer with eight —$C(O)CH_2OCH_2CH_2OCH_2CH_2NH$—$C(O)C(CH_3)$═N—O—$CH_2$—C(O)— Insulin groups conjugated to the dendrimer.

"AoA-LYRAG" refers to a LYRAG ligand functionalised with AoA.

"G-1 D" refers to a generation 1 dendrimer.

"G-1 D (Pyr)$_n$" refers to a generation 1 dendrimer with a valency of n functionalised with Pyr surface groups "Pyruvate dendrimers" or "pyrunate-functionalised dendrimers" refers to dendrimers which have surface groups which comprise $-L^1$, wherein $-L^1$ is —$C(O)C(O)CH_3$, "AoA peptides" refers to peptides which comprise $-L^2$, wherein $-L^2$ is —C(O)—$CH_2$—O—$NH_2$.

EXAMPLES

Experimental procedures

General Methods

Unless stated otherwise, all solvents and other chemicals were obtained from commercial sources and used as received. PAMAM dendrimers with amino surface groups were supplied by Sigma-Aldrich and Dendritic Nanotechnologies (Mount Pleasant, Mich., U.S.A). Analytical reverse phase high pressure liquid chromatography (HPLC) was performed on a Waters 2795 HPLC module coupled with 214 nm UV detection, using a Macherey Nagel 300A, 5 μm C8 column. Preparative HPLC was performed on a Delta 600 module coupled with a 2487 UV detector using a Vydac C8 column (250×22 mm i.d., 10 μm particle size) under previously described conditions (Gaertner, H., Offord, R., Botti, P., Kuenzi, G., and Hartley, O. (2008) Semisynthetic Analogues of PSC-RANTES, a Potent Anti-HIV Protein. *Bioconjug Chem* 19, 480-9.). Electrophoresis of peptide and protein constructs was performed on NuPage 12% Bis-Tris Gel from Invitrogen (MOPS buffer, 100 V). Matrix-assisted laser desorption/ionization time of flight mass spectrometry (MALDI-TOF-MS) spectra were obtained on a Perspective Biosystems Voyager SSTR or on a Shimadzu AXIMA CFR Plus mass spectrometer using sinapinic acid, 2,5 dihydroxybenzoic acid or 2',4',6'-trihydroxyacetophenonemonohydrate as matrix. Electrospray ionization mass spectrometry (ESI-MS) spectra were measured on either a MicroMass Quattro Micro Mass Spectrometer or a Waters Q-TOF Ultima Mass Spectrometer, both used in positive ionization mode.

Generation of Pyruvate Dendrimers (i) Succinimide Activated Pyruvate (Pyruvate-OSu)

Pyruvate succinimide ester was prepared by activation of pyruvic acid (50 mg/ml) with 1 equivalent dicyclohexylcarbodiimide and 1 equivalent N-hydroxysuccinimide in $CH_2Cl_2$. The mixture was stirred overnight and filtered to remove the dicyclohexylurea precipitate. The solvent was evaporated using reduced pressure and the powder obtained was used without further purification.

(ii) PEG-Elongation of Dendrimer Arms

Where required, dendrimer arms were elongated with Boc-amino-PEG-COOH chains (either 2-[2-(Boc-amino)ethoxy]ethoxyacetic acid (Boc-AEEA) or Boc-15-amino-4,7,10,13-tetraoxapentanedecanoic acid (Boc-ATOPA)), activated by esterification with pentafluorophenol.

A synthetic approach that ensures a high degree of monodispersity of PEGylated material was developed. Surface amino groups were fully capped with PEG chains of varying molecular weight (MW 265 and 5000).

Modification with Boc 15-Amino4,7,10,13-tetraoxapentanedecanoic acid (Boc-ATOPA).

In a typical experiment, Boc-ATOPA-Opfp (210 mg, 390 µmol) in 0.6 mL DCM was added to $G3(NH_2)_{32}$ (40 mg, 5.8 µmol) in 0.4 mL MeOH, followed by N-methylmorpholine (43 µL, 0.39 mmol) and incubated overnight at room temperature. Complete acylation of the dendrimer was checked by ninhydrin test. The Boc-protected material was purified on a LH20 column equilibrated in MeOH; material recovered: 80 mg. The material is then Boc-deprotected in neat TFA, dried and purified by preparative HPLC; material recovered: 60 mg.

Modification with Boc-$PEG_{5kD}$-NHS

To a stirred mixture of $PEG_{5kD}$-NHS ester (280 mg, 56 µmol) in DMF:DMSO (1:1, v:v; 0.6 mL) was added $G3(NH_2)_{32}$ (4 mg, 0.58 µmol) followed by Diisopropyl ethylamine (DIEA, 10 µL, 0.056 mmol) and PyBop (32 mg, 0.06 mmol) solubilised in 0.1 mL. The reaction mixture was left to stir for 24 h at room temperature under nitrogen. Complete acylation of the dendrimer was checked by ninhydrin test. The reaction mixture was poured into water (10 mL). The solution was extensively dialysed against water (10 kDa cut-off) and then concentrated on a 5 kDa ultrafree membrane and the concentration step repeated several times until complete disappearance of any trace of free PEG in the eluent. The material was freeze-dried (material recovered, 51 mg). The material is then Boc-deprotected in neat TFA (2 mL), dried, resolubized in water and freeze dried. This material with amino surface groups is ready for further functionalization as starting $G3(NH_2)_{32}$.

(iii) Functionalisation of Dendrimer Surface Groups with Pyruvate

The dendrimer solution obtained from the supplier (20% w:v in MeOH) was diluted with 9 volumes of $CH_2Cl_2$ containing 5 equivalents of pyruvate-OSu per amino group. The solution was stirred overnight at room temperature and reaction completion was verified by the Kaiser test (Kaiser, E., Colescott, R. L., Bossinger, C. D., and Cook, P. I. (1970) Color test for detection of free terminal amino groups in the solid-phase synthesis of peptides. *Analytical biochemistry* 34, 595-598). The solution was then concentrated under reduced pressure and the material resolubilized in $CH_3CN$:water (1:1 v/v) containing 0.1% w/v trifluoroacetic acid (TFA). The soluble fraction was further purified by preparative HPLC, using a gradient from 0% to 50% B buffer over 50 min, at 15 ml/min.

Conjugation of Pyruvate-Functionalised Dendrimers with Aminooxy-Functionalized Peptides and Insulin (i) Aminooxy Activated Ligands The linear peptides LYRAG (Leu-Tyr-Arg-Ala-Gly) and the measles virus haemagluttenin-derived peptide MVHA49-72 (Leu-Ile-Gly-Leu-Leu-Ala-Ile-Ala-Gly-Ile-Arg-Leu-His-Arg-Ala-Ala-Ile-Tyr-Thr-Ala-Glu-Ile-His-Lys) were synthesized according to standard automated techniques as previously described (Gaertner et al. Bioconjug Chem, 19, 480-9). They were substituted at their α-amino groups with the aminoxyacetyl group (AoA), protected with the Boc function by reaction with Boc-aminooxyacetyl-OSu. AoA-$Phe^{B1}$-insulin was prepared according to standard techniques (Rose, K., Zeng, W., Regarney, P. O., Chemushevich, I. V., Standing, K. G., and Gaertner, H. F. (1996) Natural peptides as building blocks for the synthesis of large protein-like molecules with hydrazone and oxime linkages. *Bioconjug Chem* 7, 552-6.). The derivatized products were single components on HPLC and had the expected mass spectra when analyzed by ESI-MS.

(ii) Oxime-Bond Forming Condensation Reaction

Unless otherwise stated, conjugation experiments were performed in a 0.1 M acetate buffer containing 20% $CH_3CN$ (v:v) or 8 M urea and 0.1 M anilinium acetate, pH 4.6. AoA-derivatized products (1.5-2.0 equivalents) were mixed with 1 equivalent of pyruvate dendrimer and the reaction was allowed to proceed at room temperature for 20-40 h. The conjugation products were isolated by HPLC or, in the case of MVHA (49-72) conjugates, by dialysis.

Results (i) Pyruvate Conjugation of Dendrimers

Pyruvate dendrimers were successfully synthesized by acylation of the amine terminal groups of G-1, G-2 and G-3 PAMAM dendrimers with succinimide-activated pyruvate to yield G-1$(Pyr)_8$, G-2$(Pyr)_{16}$ and G-3$(Pyr)_{32}$. Pyruvate acylation was also carried out on dendrimers of which the arms had been elongated through acylation with the amino-PEG-acids 2-[2-(Boc-amino)ethoxy]ethoxyacetic acid (Boc-AEEA) and Boc-15-amino-4,7,10,13-tetraoxapentanedecanoic acid (Boc-ATOPA) to yield G-1(AEEA-Pyr)$_8$ and G-2(ATOPA-Pyr)$_{16}$.

All pyruvate conjugation reactions went to completion as determined by the ninhydrin test for remaining free amines. The resulting pyruvate dendrimers had the expected masses (Table 1) except that the G-2$(Pyr)_{16}$ and G-3$(Pyr)_{32}$ pyruvate dendrimers gave ESI-MS data consistent with contaminating products of 200 Da lower mass than the expected value. These lower-mass products are most likely derived from lower-valency contaminants in the starting material. A loss of 200 Da corresponds not just to the lack of two pyruvate units but to the absence of two complete —($NHCH_2CH_2NH$-pyruvate) units. Such contamination of higher generation dendrimers with material lacking two terminal amine groups has been described (Wolter et al. *Biomacromolecules* 2, 1052-4). The phenomenon is thought to be due to the formation of an intramolecular bis-amide instead of the addition of two ethylene diamines during manufacture.

TABLE 1

Mass spectrometric characterization of pyruvate-conjugated dendrimers.

| Dendrimer | Calculated average Mass (Da) | Observed Mass (Da) ESI-MS |
|---|---|---|
| G-1$(Pyr)_8$ | 1990.4 | 1990.4 ± 0.4* |
| G-2$(Pyr)_{16}$ | 4377.0 | 4376.7 ± 0.1* |
| G-3$(Pyr)_{32}$ | 9150.9 | 9170.1 ± 0.8* |

TABLE 1-continued

Mass spectrometric characterization of pyruvate-conjugated dendrimers.

| Dendrimer | Calculated average Mass (Da) | Observed Mass (Da) ESI-MS |
|---|---|---|
| G-1(AEEA-Pyr)$_8$ | 3151.8 | 3151.5 ± 0.1 |
| G-2(ATOPA-Pyr)$_{16}$ | 8333.9 | 8333.4 ± 0.5 |

*ESI-MS spectra also identified contaminating products of 200 Da lower mass than the expected value.

(ii) Optimizing Conditions for Conjugation of Proteins and Peptides

The conditions for pyruvate-dendrimer conjugation with aminooxy-functionalised peptides and proteins were first optimized using the G-1(Pyr)$_8$ dendrimer and a small model peptide, AoA-LYRAG. Carrying out the reaction at pH 4.6 results in the formation of a mixture of conjugates containing mainly partially substituted intermediates and only traces of the fully substituted octamer (FIG. 1A). When the reaction is carried out at pH 4.6 in the presence of 0.1 M aniline, however, the reaction goes to completion, yielding the fully substituted octamer (FIG. 1B).

The conditions for pyruvate-dendrimer conjugation with aminooxy-functionalised peptides and proteins were also carried out using G2(Pyr)$_{16}$ and G3(Pyr)$_{32}$ dendrimers and EGSREQDWE and insulin, as described in (vi) below.

(iii) Evaluation of Mass Spectrometric Characterization Methods

Figure 2A:
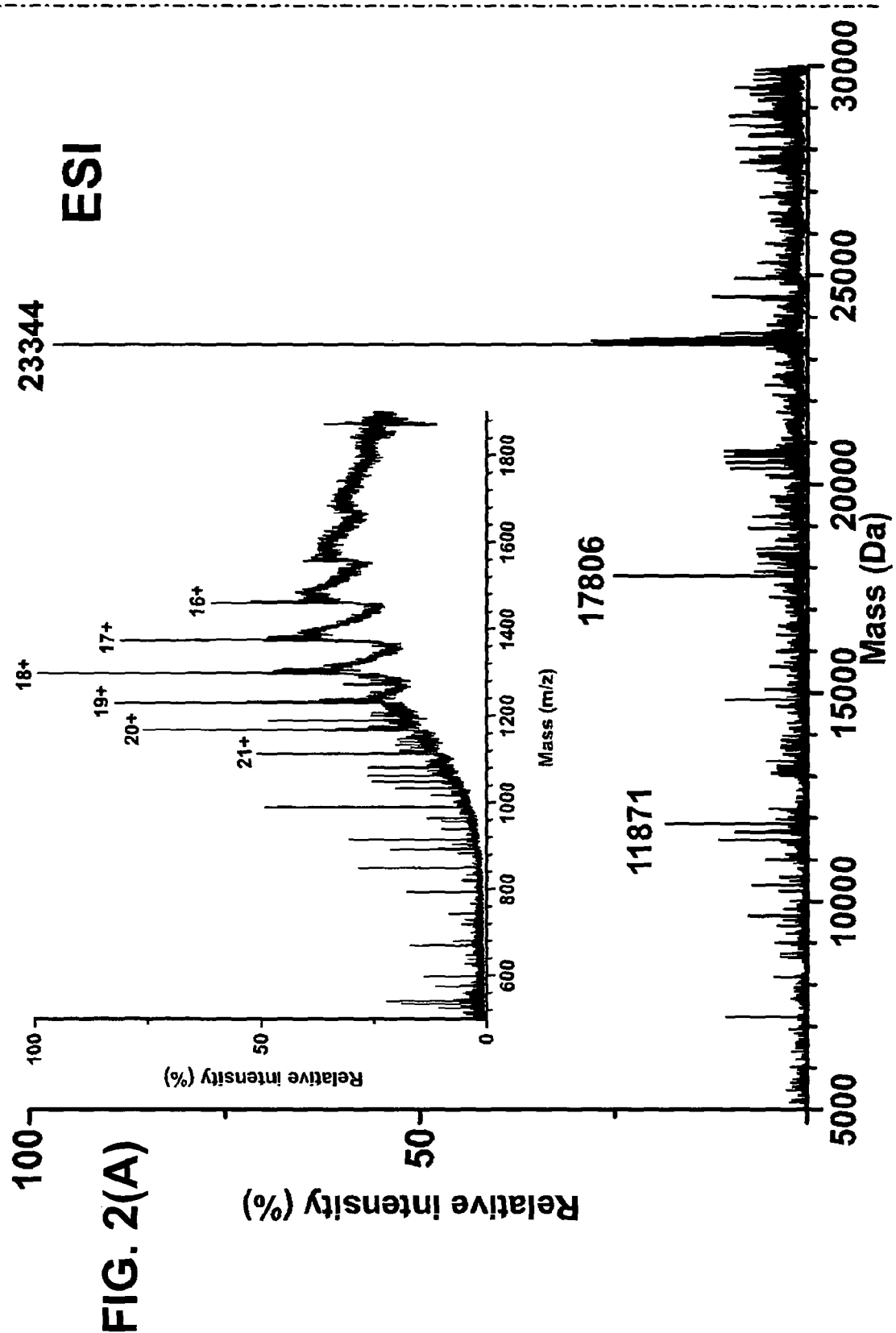
FIG. 2 shows experimental and deconvoluted ESI-TOF-MS of G-1(AEEA-PyrAoA-MVHA49-72)$_8$ (A) and G-1 (AEEA-Pyr=AoA-Insulin)$_8$ (B) as compared with MALDI-TOF-MS. While ESI-TOF-MS analysis indicates that the samples predominantly contain fully decorated dendrimer with no traces of lower substituted contaminants, MALDI-TOF-MS analysis of the same samples reveals a mass component corresponding to the fully substituted dendrimer, plus mass components corresponding to the dendrimer lacking one, two and three substituent moieties. The absence of the lower mass components in the ESI-TOF mass spectra indicates that the lower mass peaks in the MALDI-TOF mass spectra do not correspond to incompletely decorated dendrimers but artefacts resulting from the destructive effect on the oxime bonds of the MALDI laser pulses.
Figure 2B:
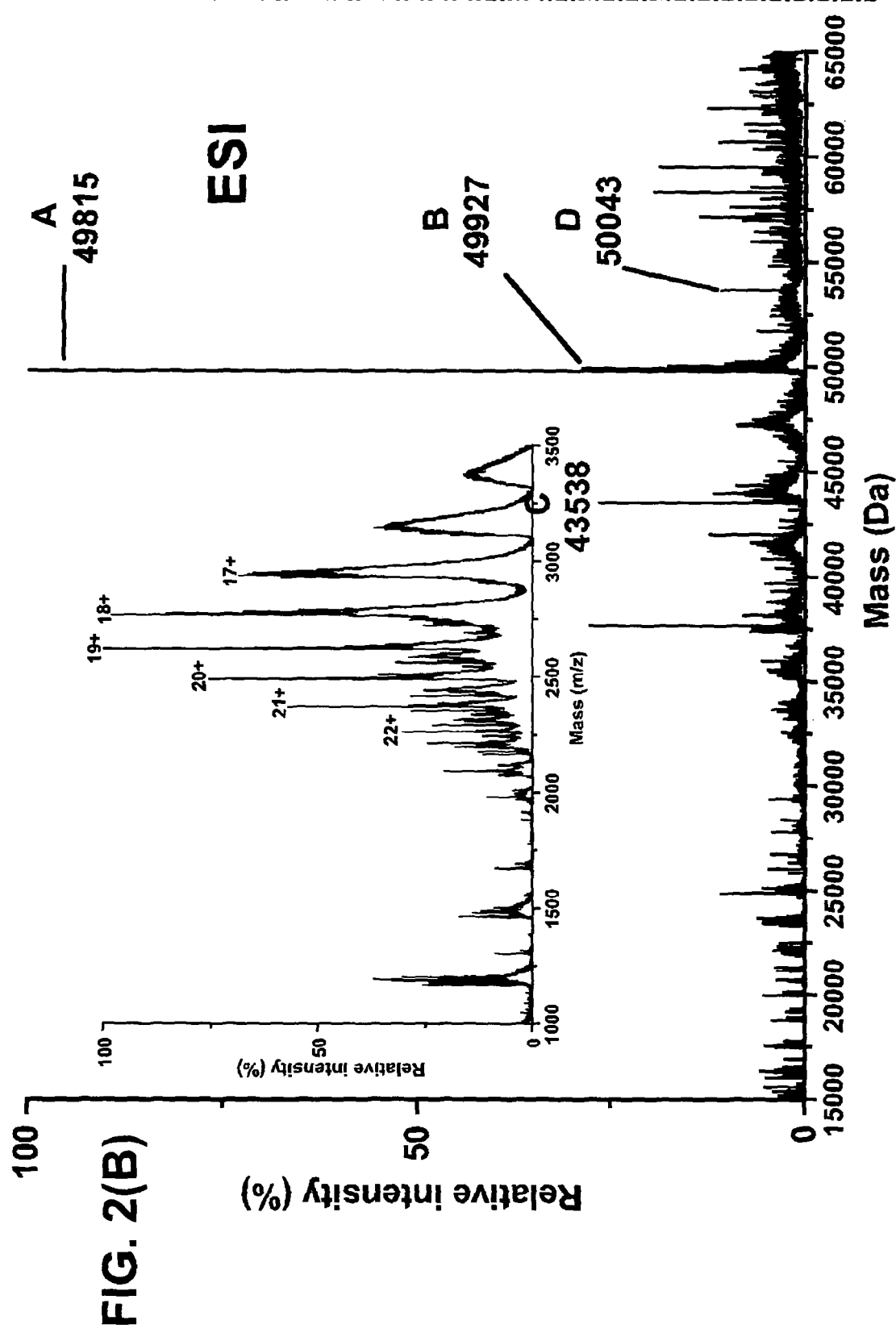

Characterization of complex dendrimers with large peptide and protein substituents presents a methodological challenge, and the inventors opted to evaluate ESI-TOF-MS (electrospray ionization time of flight mass spectrometry) and MALDI-TOF-MS as characterization tools. As reference materials the inventors used the octameric dendrimers resulting from the decoration of G-1(Pyr)$_8$ dendrimers with either AoA-MVHA49-72, yielding G-1(Pyr=AoA-MVHA49-72)$_8$, or AoA-insulin, yielding G-1(AEEA-Pyr=AoA-Insulin)$_8$. ESI-TOF-MS (FIG. 2A) clearly indicated that in both cases the major component in the reaction mixture was indeed the fully decorated octamer (for AoA-MVHA49-72 observed average mass 23343.8±0.7 Da, calculated mass 23344.5 Da; for AoA-insulin observed average mass 49809±5 Da, calculated mass 49821.2 Da). The absence in the mixture of detectable levels of incompletely decorated material is indicative of the homogeneity of the reaction products. Analysis of the same material by MALDI-TOF-MS (FIG. 2B) revealed peaks corresponding to the expected masses of the fully decorated octamers (observed average mass 23401 Da for AoA-MVHA49-72; observed mass 48862 Da for AoA insulin) plus a series of peaks corresponding to the expected masses minus multiples of the mass of the substituent moiety (i.e. approximately 2700 Da for MHVA(49-71) and 5800 Da for insulin). The absence of these lower mass species in the ESI-TOF mass spectra indicates that they do not correspond to incompletely decorated dendrimers but artefacts resulting from the destructive effect on the oxime bonds of the MALDI laser pulses, as described previously (Nardin, E. H., Calvo-Calle, J. M., Oliveira, G. A., Clavijo, P., Nussenzweig, R., Simon, R., Zeng, W., and Rose, K. (1998) *Plasmodium falciparum* polyoximes: highly immunogenic synthetic vaccines constructed by chemoselective ligation of repeat B-cell epitopes and a universal T-cell epitope of CS protein. *Vaccine* 16, 590-600). Hence while ESI-TOF-MS has the advantage of being a non-destructive characterization method for the dendrimers in this study, it has the drawback of having, at least in our case, a ceiling size limit for detection at around 50 kDa. On the other hand, while MALDI-TOF-MS has the advantage of being able to detect dendrimers of higher mass, analysis of the results obtained should take account of the destructive effect of the laser pulses on oxime bonds.

(iv) Synthesis of Peptide and Protein-Conjugated Dendrimers

The optimized oxime conjugation conditions were used to decorate a wider range of dendrimers (up to G-3), with or without arms extended by short PEG spacers, using the short LYRAG peptide, the longer measles virus haemagluttenin (49-72) peptide and recombinant insulin. The reaction products were characterized by mass spectrometry (Table 2).

TABLE 2

Peptide and insulin dendrimers obtained by aniline catalyzed oxime bond formation.

| Dendrimer | Calculated average Mass (Da) | Observed average Mass (Da) ESI-MS, ESI-TOF-MS | Observed average Mass (Da) MALDI-TOF-MS |
|---|---|---|---|
| G-1(Pyr = AoA-LYRAG)$_8$ | 7060.2 | 7060.1 ± 0.3 | 7061 |
| G-2(Pyr = AoA-LYRAG)$_{16}$ | 14516.6 | 14517.4 ± 1.1 | 14520 |
| G-3(Pyr = AoA-LYRAG)$_{32}$ | 29430.3 | nd | Envelope of 16000-29500 |
| G-1(AEEA-Pyr = AoA-LYRAG)$_8$ | 8221.6 | 8221.5 ± 0.6 | nd |
| G-2(ATOPA-Pyr = AoA-LYRAG)$_{16}$ | 18473.6 | 18472.6 ± 0.8 | nd |
| G-1(Pyr = AoA-MVHA49-72)$_8$ | 23344.5 | 23344.4 ± 0.7 | 23450 ± 250 |
| G-2(Pyr = AoA-MVHA49-72)$_{16}$ | 47113.3 | nd | 47200 ± 2003 |
| G-3(Pyr = AoA-MVHA49-72)$_{32}$ | 94594.7 | nd | Envelope of 56000-95000 |
| G-1(AEEA-Pyr = AoA-Insulin)$_8$ | 49821.2 | 49815.0 ± 1.0 | 49970 ± 500 |
| G-2(ATOPA-Pyr = AoA-Insulin)$_{16}$ | 101672.8 | nd | 101500 ± 1000 |
| G-1(Pyr = AoA-Insulin)$_8$ | 48659.8 | nd | 48700 ± 100 |
| G-2(Pyr = AoA-Insulin)$_{16}$ | 97743.8 | nd | 98000 ± 1000 |
| G-3(Pyr = AoA-Insulin)$_{32}$ | 195855.8 | nd | Envelope of 130000-190000 |

All MALDI-TOF-MS mass determinations contain signals (probably artifactual resulting from the destructive effect of the MALDI laser pulses on the oxime as these lower mass species are not present in the ESI-TOF mass spectra) attributable to lower substituted constructs (nd; not determined).

These results indicate that the optimized oxime procedure yields fully decorated dendrimers from G-1 to G-3 either with or without PEG-extended arms and using three different aminooxy conjugated substituents. While the MALDI-TOF-MS spectra included signals corresponding to lower-substituted products, these would be expected to be due at least in part to the destructive effect of the laser desorption on oxime bonds (FIG. 2).

(v) Characterization of Insulin Dendrimers by SDS-PAGE

Figure 3:
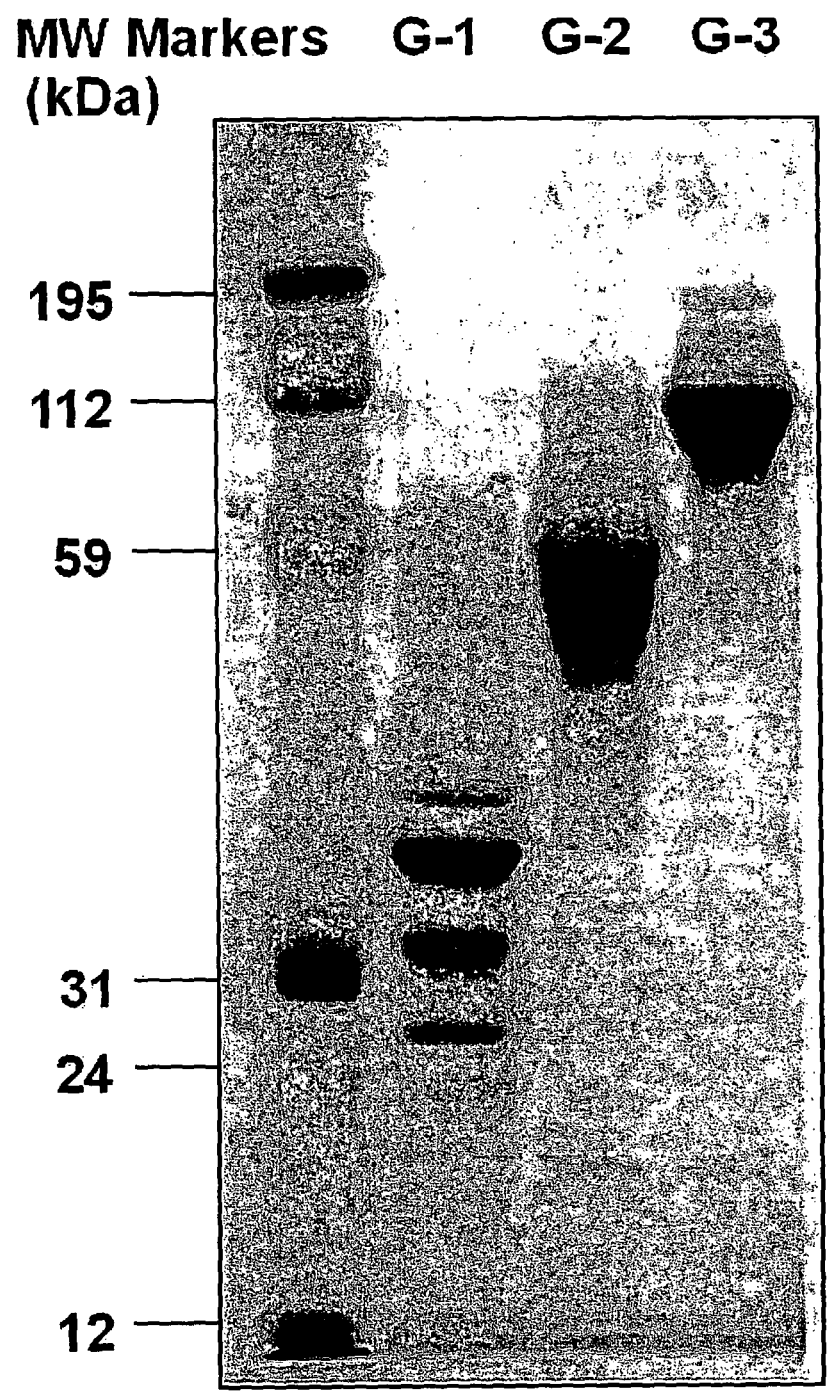
FIG. 3 shows SDS-PAGE analysis of G-1(PyrAoA-Insulin)$_8$, G-2(PyrAoA-Insulin)$_{16}$ and G-3(Pyr=AoA-Insulin)$_{32}$ (indicated as G1, G-2 and G-3) indicating that dendrimer samples from each reaction show very limited dispersity. The tight clustering bands close to the slowest migrating species, together with the absence of bands corresponding to unsubstituted material provides evidence of the high homogeneity of the decorated dendrimer samples.

In order to further investigate the homogeneity of the dendrimer products, SDS-PAGE was used to analyse a series of insulin-decorated dendrimers of increasing complexity: G-1 (Pyr=AoA-Insulin)$_8$, G-1(PyrAoA-Insulin)$_{16}$ and G-1 (Pyr=AoA-Insulin)$_{32}$ (FIG. 3). Each sample appeared on the gel as a slower-migrating major component together with a relatively few minor bands. Based on the mass spectrometric analysis of the same samples (Table 2), the major components most likely correspond to the fully decorated dendrimers. If this is the case, it would imply that size-dependent migration of the dendrimers on SDS-PAGE is not proportional to that of the globular protein markers, with the fully decorated G-1, G-2 and G-3 dendrimers, which have calculated masses of approximately 49, 98 and 196 kDa, respectively, migrating at positions corresponding to approximately 36, 50 and 100 kDa.

Comparison of the appearance of the G-1(PyrAoA-Insulin)$_8$ sample on the gel with the corresponding ESI-TOF mass spectrum (FIG. 2) indicates that sample treatment prior to gel loading is partially destructive. This is mostly likely because heating the samples in gel loading buffer led to brief exposure to basic pH levels at which oxime bonds are labile. Despite this, the tight clustering bands close to the slowest migrating species, together with the absence of bands corresponding to unsubstituted material provides further evidence of the high homogeneity of the decorated dendrimer samples.

(vi) Further Conjugation of Proteins and Peptides

In order to further demonstrate the role of the anilinium acetate catalyst in the dendrimer oximation reaction, the extent of dendrimer scaffold decoration achieved under different experimental conditions was determined. The following experiments were, unless otherwise stated, performed in accordance with the procedures described above.

Generation 2 and 3 pyruvate dendrimers, G2(Pyr)$_{16}$ and G3(Pyr)$_{32}$ were incubated with: (a) AoA-derivatized 9-mer peptide EGSREQDWE; and (b) AoA-derivatized insulin; under conditions where peptide/protein is in 2-fold excess over dendrimer pyruvate equivalents.

Reactions were carried out overnight at room temperature under different experimental conditions:
1M sodium formate in 8 M urea, pH 3.0
1M sodium acetate in 8 M urea, pH 4.6
1M sodium acetate, 0.1 M anilinium acetate in 8 M urea, pH 4.6.

Product mixtures were then analyzed by RP-HPLC, with the conjugation product peak collected and characterized by MALDI-TOF.

(a) Conjugation of 9-Mer Peptide EGSREQDWE

HPLC profiles show that for the peptide-dendrimer conjugates, the reaction goes almost to completion in the presence of aniline with a major shift of the peak corresponding to the conjugate towards the right, i.e. more extensive decoration (FIG. 4).

Figure 5A:
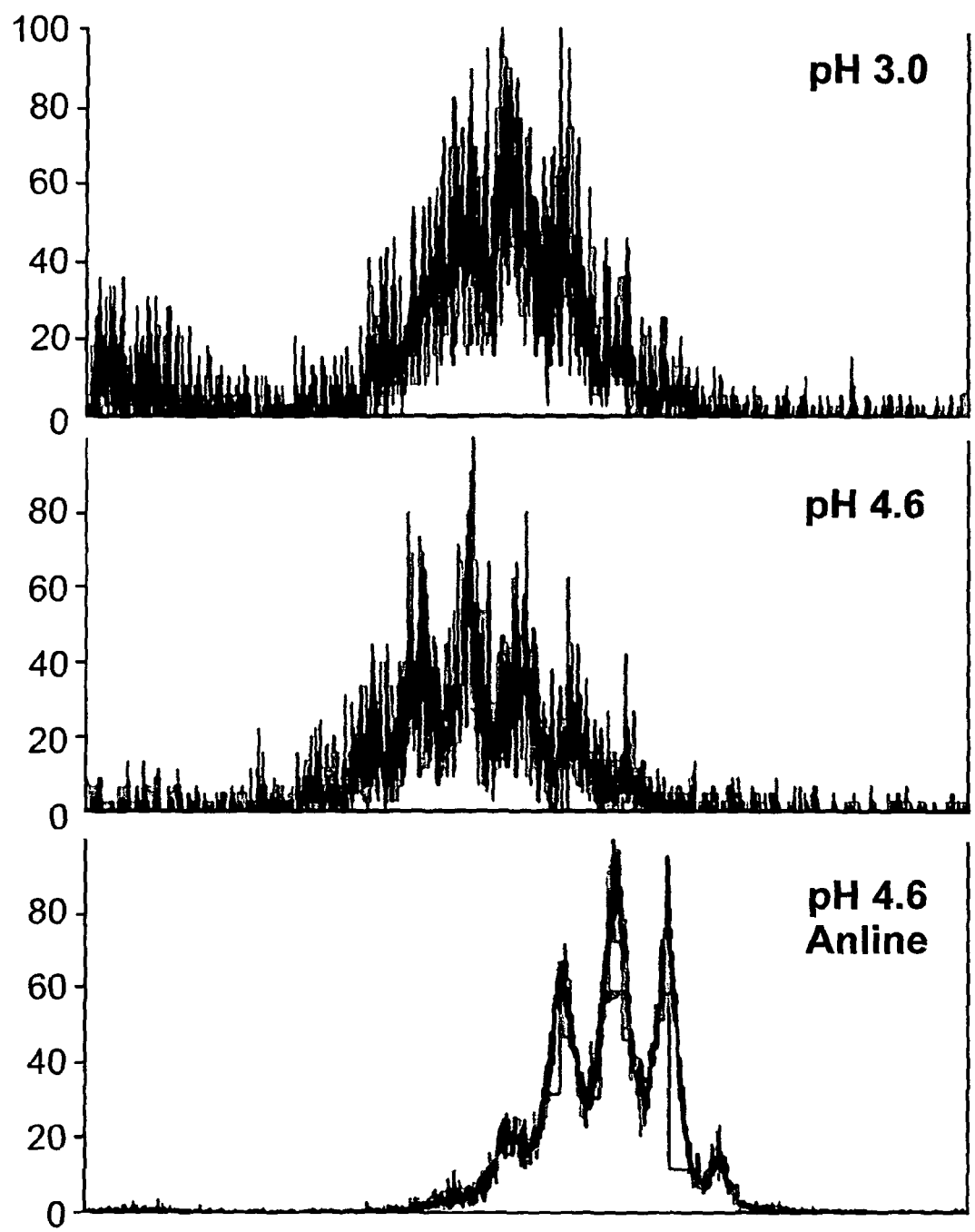
FIG. 5A shows that the fully decorated conjugate (MW=23448) is only obtained at pH 4.6 with aniline. The product masses for the G3-(EGSREQDWE)$_{32}$ dendrimers were not precisely resolved, but the results show a clear trend towards more complete decoration and lower heterogeneity in the presence of the aniline catalyst (FIG. 5B).
Figure 5B:
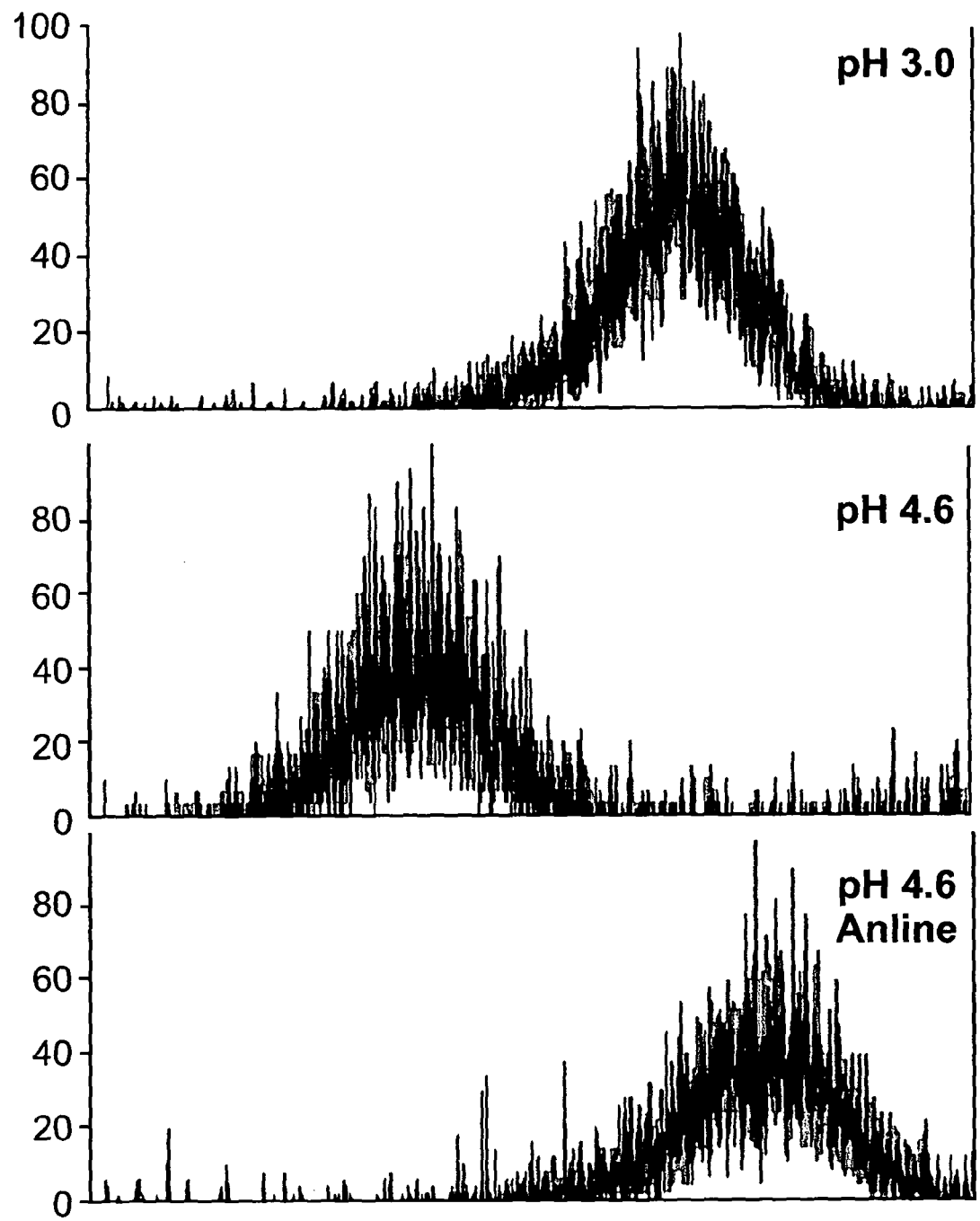
FIG. 5 shows MALDI-TOF characterization of the collected conjugate peaks shown in FIG. 4, i.e. (A) G2-(Pyr=AoA-EGSREQDWE)$_{16}$ (theoretical mass=23448), and (B) G2-(Pyr=AoA-EGSREQDWE)$_{32}$ obtained under the different conditions indicated. The result of more extensive decoration is confirmed since

This result was confirmed by the MALDI-TOF characterization of the collected conjugate peaks, where in the case of G2-(EGSREQDWE)$_{16}$, the fully decorated conjugate (M W=23448) is only obtained at pH 4.6 with aniline; under the other conditions the highest MW is lower than the target mass and the product masses are more heterogenous (FIG. 5A). The product masses for the G3-(EGSREQDWE)$_{32}$ dendrimers were not precisely resolved, but the results show a clear trend towards more complete decoration and lower heterogeneity in the presence of the aniline catalyst (FIG. 5B).

(b) Conjugation of Insulin

Figure 6:
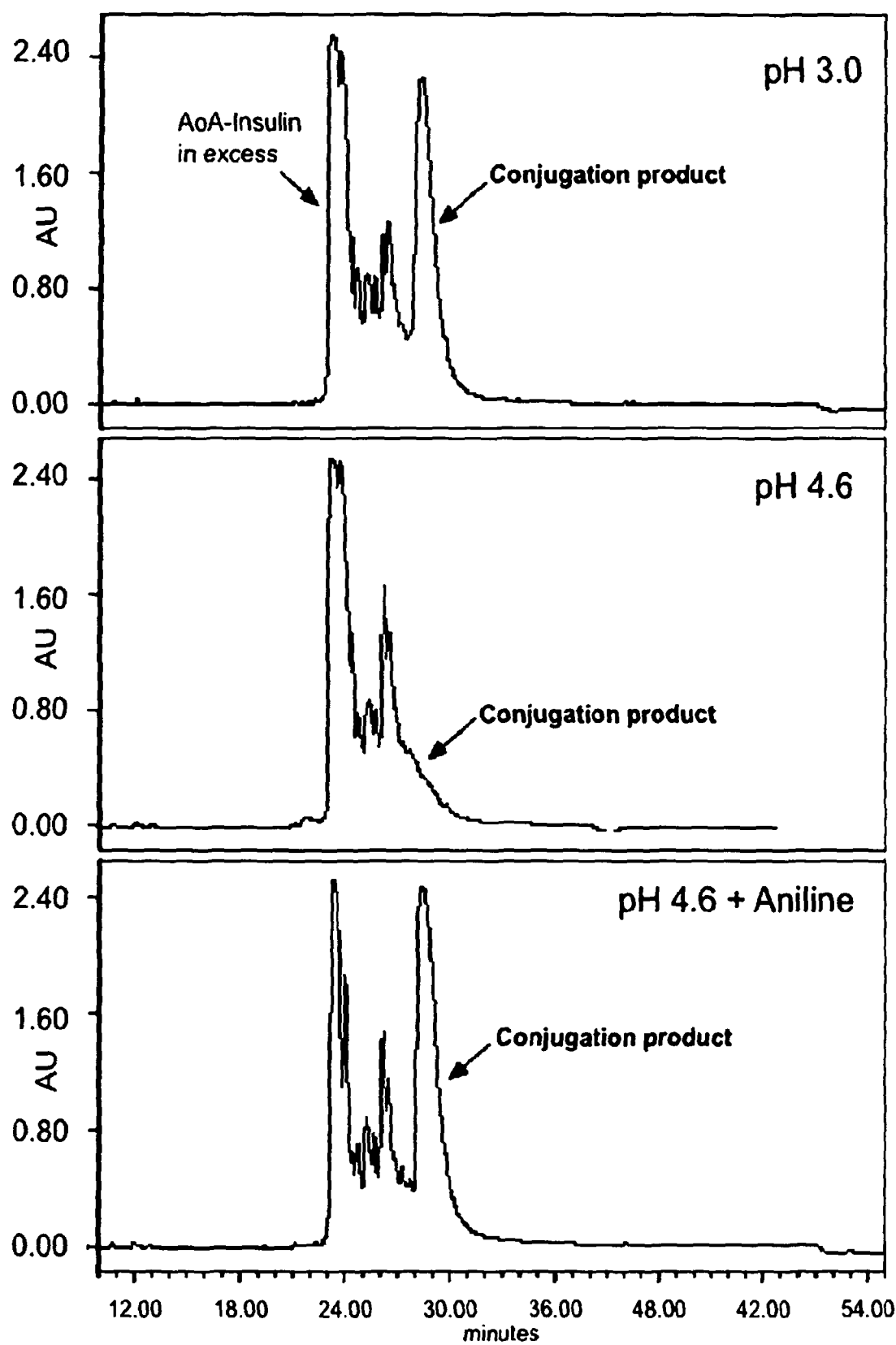
FIG. 6 shows rp-HPLC analysis of conjugation of AoA-insulin with G3-(Pyr)$_{32}$ after 20 h incubation under different reaction conditions as indicated: 1M sodium formate in 8 M urea, pH 3.0; 1M sodium acetate in 8 M urea, pH 4.6; and 1M sodium acetate, 0.1 M anilinium acetate in 8 M urea, pH 4.6.
Figure 7:
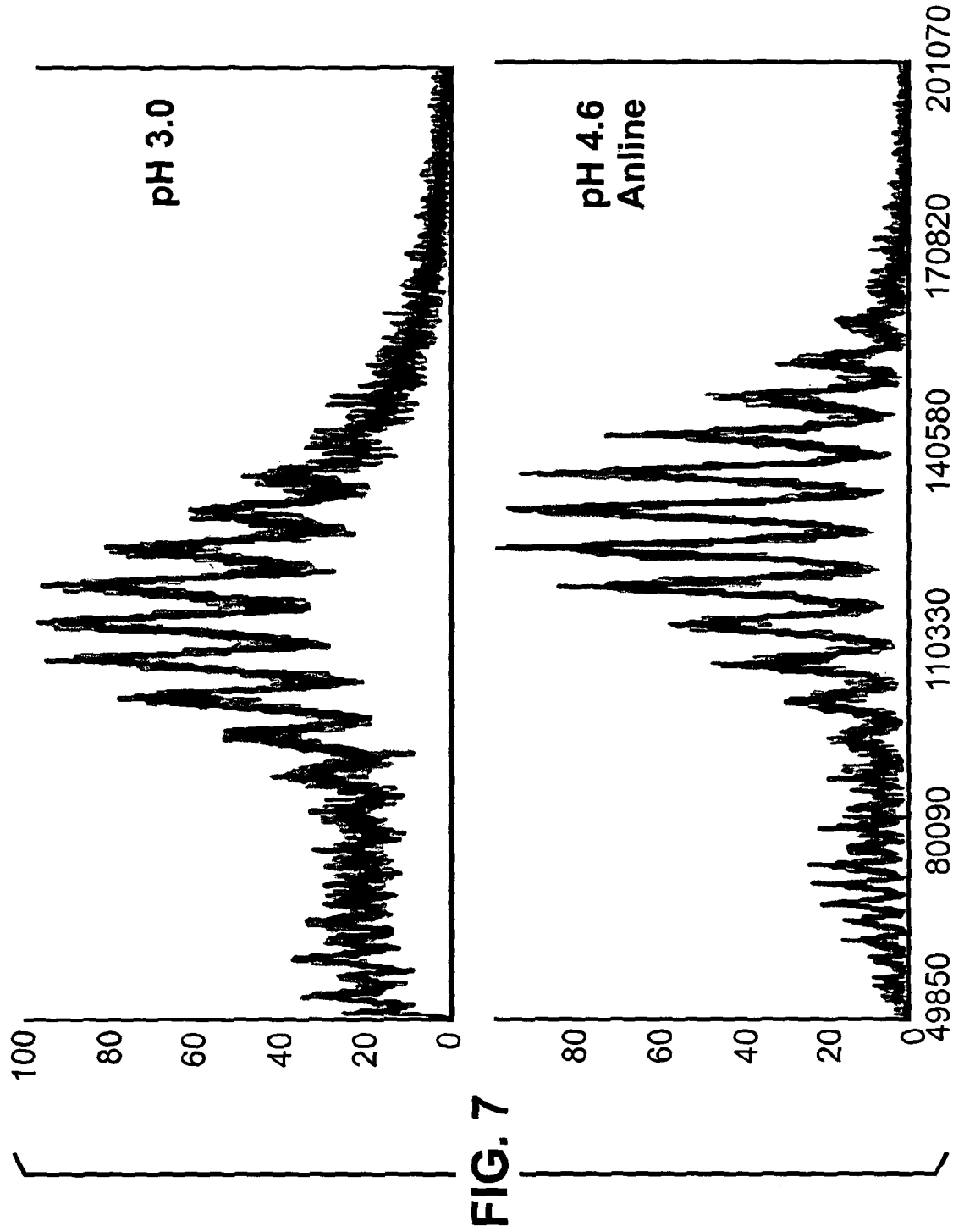
FIG. 7 shows MALDI-TOF characterization of the collected product peaks shown in FIG. 6, i.e. G3-(Pyr=AoA-Insulin)$_{32}$ (theoretical mass=195855) obtained under the conditions indicated. The degree of decoration of the G3(Insulin)$_{32}$ dendrimer is shown to be significantly higher at pH 4.6 in the presence of aniline than without aniline at pH 3.0.

For the insulin dendrimer conjugates, rp-HPLC analysis apparently indicates that decoration at pH 3.0 in the absence of aniline occurs to a comparable extent to decoration at pH 4.6 in the presence of aniline (FIG. 6). However this is a reflection of the limits of rp-HPLC to resolve different decorated species. MALDI-TOF mass spectrometry of collected product peaks revealed that the degree of decoration of the G3(Insulin)$_{32}$ dendrimer is significantly higher at pH 4.6 in the presence of aniline than without aniline at pH 3.0 (FIG. 7).

The invention claimed is:

1. A method for preparing a decorated macromolecular scaffold comprising the step of reacting the surface groups of a macromolecular scaffold with ligands to form oxime or hydrazone bonds between the surface groups of the macromolecular scaffold and the ligands, wherein the reaction is carried out in the presence of an aniline or substituted aniline catalyst and
    (i) the surface groups on the macromolecular scaffold comprise groups -E$^1$-L$^1$; and
    (ii) the ligands each comprise group -E$^2$-L$^2$;
    wherein E$^1$ and E$^2$ are independently each optional linkers;
    wherein one of -L$^1$ or -L$^2$ is —C(O)—Z$^1$—C(O)R$^1$ and the other of -L$^1$ and -L$^2$ is —C(O)—Z$^2$—X—NH$_2$;
    wherein Z$^1$ is selected from (CH$_2$)$_n$ or

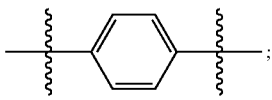

wherein Z$^2$ is selected from (CH$_2$)$_n$,

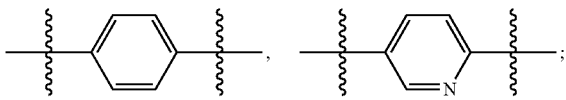

or —NH—NHC(O)—;
n is 0, 1, 2 or 3;
R$^1$ is H or CH$_3$;
X is NH or O; and
wherein -L$^1$ and -L$^2$ react to form —C(O)—Z$^1$—C(R$^1$)=N—X—Z$^2$—C(O)—; and further comprising the step of
    (iii) reacting a macromolecular scaffold to introduce group -E$^1$-L$^1$; and/or
    (iv) reacting ligands to introduce groups -E$^2$-L$^2$;
    wherein step (iii) comprises reacting a macromolecular scaffold with

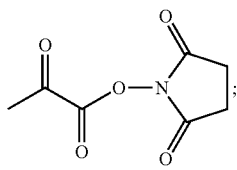

and step (iv) comprises reacting ligands with

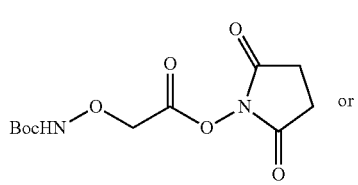

or

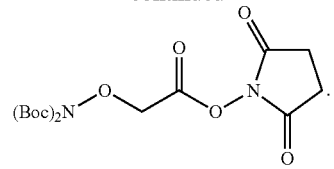

2. The method of claim 1, wherein X is O and the groups -L$^1$ and -L$^2$ react to form an oxime bond.

3. The method of claim 1 wherein
-L$^1$ is —C(O)C(O)CH$_3$; and
-L$^2$ is —C(O)CH$_2$(O)NH$_2$.

4. The method of claim 1 which optionally comprises the step of reacting a macromolecular scaffold to introduce optional linker -E$^1$.

5. The method of claim 1 wherein the macromolecular scaffold is a dendrimer.

6. The method of claim 5 wherein the dendrimer is a PAMAM dendrimer.

7. The method of claim 1 wherein the aniline or substituted aniline has a pKa of greater than 4.0.

8. The method of claim 1 wherein the ligand is a peptide or protein.

9. A method for preparing a decorated macromolecular scaffold comprising the step of reacting the surface groups of a macromolecular scaffold with ligands to form oxime or hydrazone bonds between the surface groups of the macromolecular scaffold and the ligands, wherein the reaction is carried out in the presence of an aniline or substituted aniline catalyst and
    (i) the surface groups on the macromolecular scaffold comprise groups -E$^1$-L$^1$; and
    (ii) the ligands each comprise group -E$^2$-L$^2$;
    wherein E$^1$ and E$^2$ are independently each optional linkers;
    wherein one of -L$^1$ or -L$^2$ is —C(O)—Z$^1$—C(O)R$^1$ and the other of -L$^1$ and -L$^2$ is —C(O)—Z$^2$—X—NH$_2$;
    wherein Z$^1$ is selected from (CH$_2$)$_n$, or

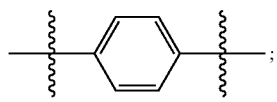

wherein Z$^2$ is selected from (CH$_2$)$_n$,

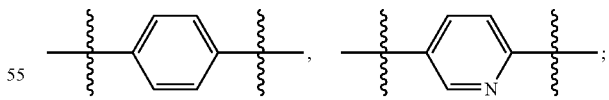

or —NH—NHC(O)—;
n is 0,1,2 or 3;
R$^1$ is H or CH$_3$;
X is NH or O; and
wherein -L$^1$ and -L$^2$ react to form —C(O)—Z$^1$—C(R$^1$)=N—X—Z$^2$—C(O)—; and
wherein E$^1$ is —C(O)(CH$_2$)$_m$-PEG-NH—; wherein m is 0, 1, 2 or 3; and PEG comprises 1 to 30 repeating units of the formula —OCH$_2$CH$_2$—.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Glu Gly Ser Arg Glu Gln Asp Trp Glu
1               5

<210> SEQ ID NO 2
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 2

Leu Ile Gly Leu Ala Ile Ala Gly Ile Arg Leu His Arg Ala Ala Ile
1               5                   10                  15

Tyr Thr Ala Glu Ile His Lys
            20

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
```

```
<400> SEQUENCE: 3

Leu Tyr Arg Ala Gly
1               5
```